(12) United States Patent  
Pepper et al.

(10) Patent No.: US 8,715,310 B2  
(45) Date of Patent: *May 6, 2014

(54) NON-COMPLIANT MEDICAL BALLOON

(75) Inventors: Lanny R. Pepper, Larue, TX (US);  
Charles J. Cox, Eustace, TX (US);  
William F. Davies, Jr., Athens, TX (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/563,249

(22) Filed: Jul. 31, 2012

(65) Prior Publication Data

US 2013/0006290 A1    Jan. 3, 2013

Related U.S. Application Data

(63) Continuation of application No. 12/537,850, filed on Aug. 7, 2009, now Pat. No. 8,236,221, which is a continuation of application No. 12/187,259, filed on Aug. 6, 2008, now Pat. No. 8,002,744.

(60) Provisional application No. 60/954,252, filed on Aug. 6, 2007.

(51) Int. Cl.  
*A61M 29/00* (2006.01)  
*B29C 70/86* (2006.01)

(52) U.S. Cl.  
USPC ........... 606/192; 264/279; 264/258; 264/263; 156/189; 604/103.13

(58) Field of Classification Search  
USPC ......................... 264/319, 320, 258, 263, 279; 604/103.13–103.09, 162; 604/10.13–103.09; 606/192  
See application file for complete search history.

(56) References Cited

U.S. PATENT DOCUMENTS

| | | | | |
|---|---|---|---|---|
| 5,330,429 A * | 7/1994 | Noguchi et al. | ......... | 604/103.12 |
| 7,967,781 B2 * | 6/2011 | Simpson et al. | ......... | 604/103.04 |
| 8,313,601 B2 * | 11/2012 | Pepper et al. | ................. | 156/189 |
| 8,323,242 B2 * | 12/2012 | Beckham | ................. | 604/103.09 |
| 2006/0085024 A1 * | 4/2006 | Pepper et al. | ................. | 606/192 |
| 2012/0221038 A1 * | 8/2012 | Simpson | ........................ | 606/192 |
| 2013/0131709 A1 * | 5/2013 | Davies et al. | ................. | 606/192 |
| 2013/0190796 A1 * | 7/2013 | Tilson et al. | ................. | 606/192 |

OTHER PUBLICATIONS http://www.thefreedictionary.com/embed, (2002-HarperCollins Publisher).*

* cited by examiner

*Primary Examiner* — Joseph S Del Sole  
*Assistant Examiner* — Nahida Sultana  
(74) *Attorney, Agent, or Firm* — King & Schickli, PLLC

(57) ABSTRACT

A non-compliant fiber-reinforced medical balloon comprises a first fiber layer and a second fiber layer embedded in a continuous matrix of thermally-weldable polymer material defining a barrel wall, cone walls and neck walls. The fibers of the first fiber layer run substantially parallel to one another and substantially parallel to the longitudinal axis. The fibers of the first fiber layer have a pattern of different lengths and are divisible into a first group and a second group based on length.

7 Claims, 18 Drawing Sheets

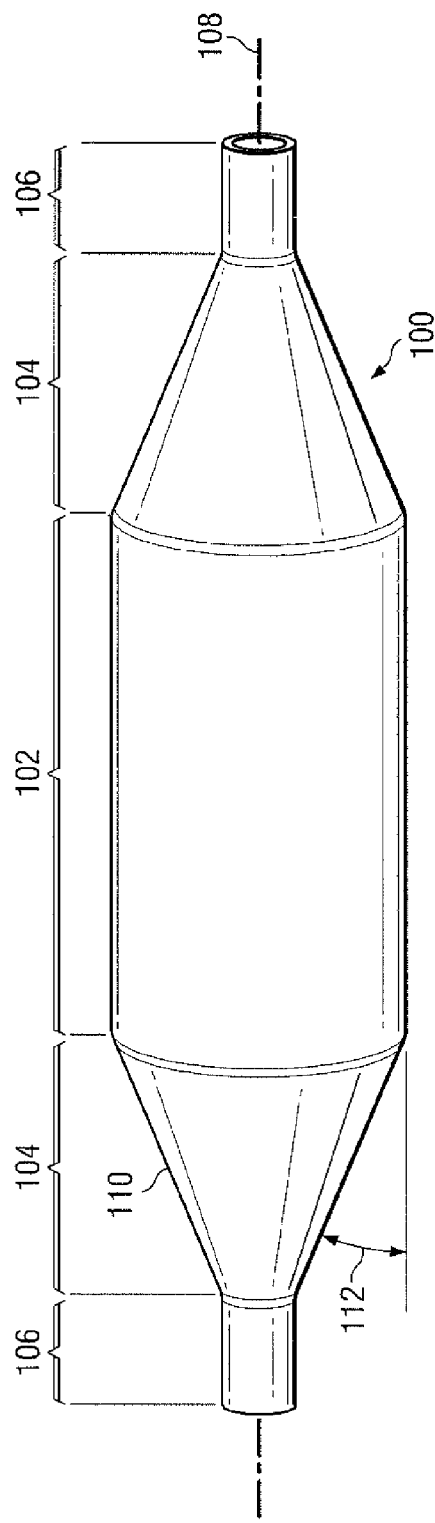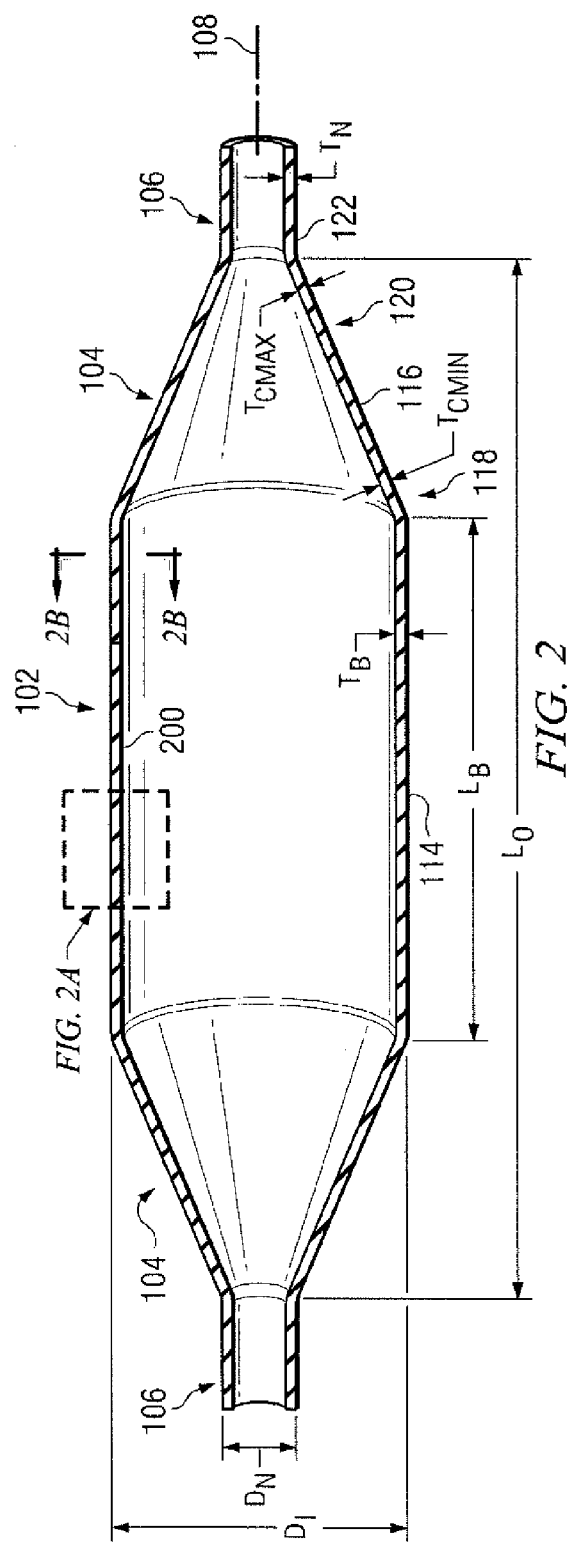

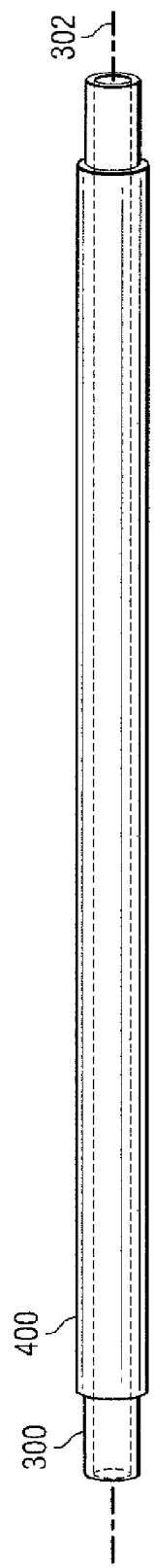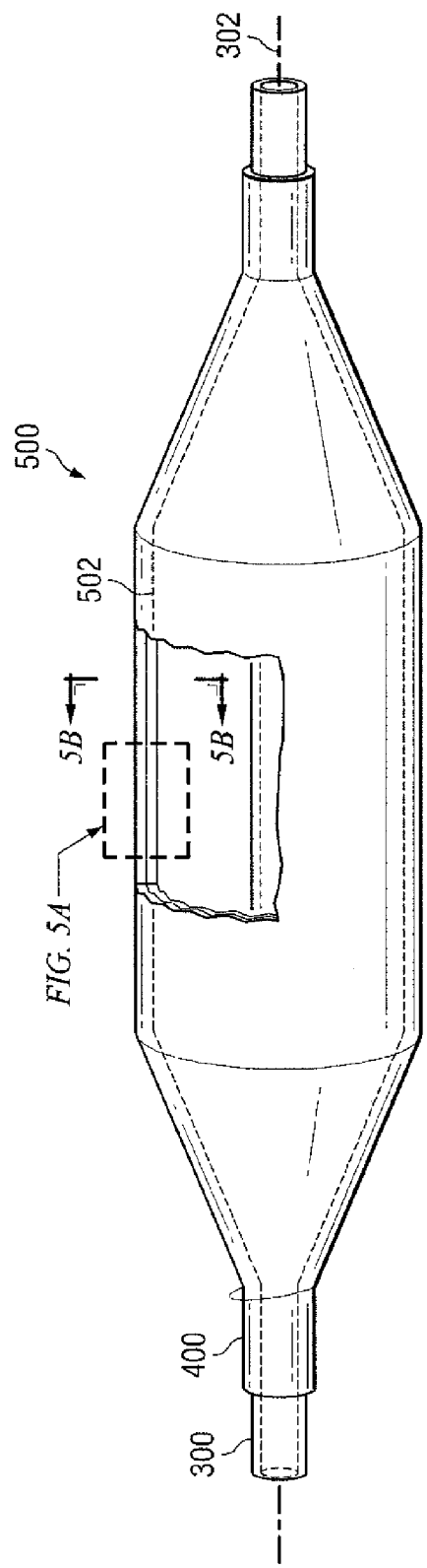

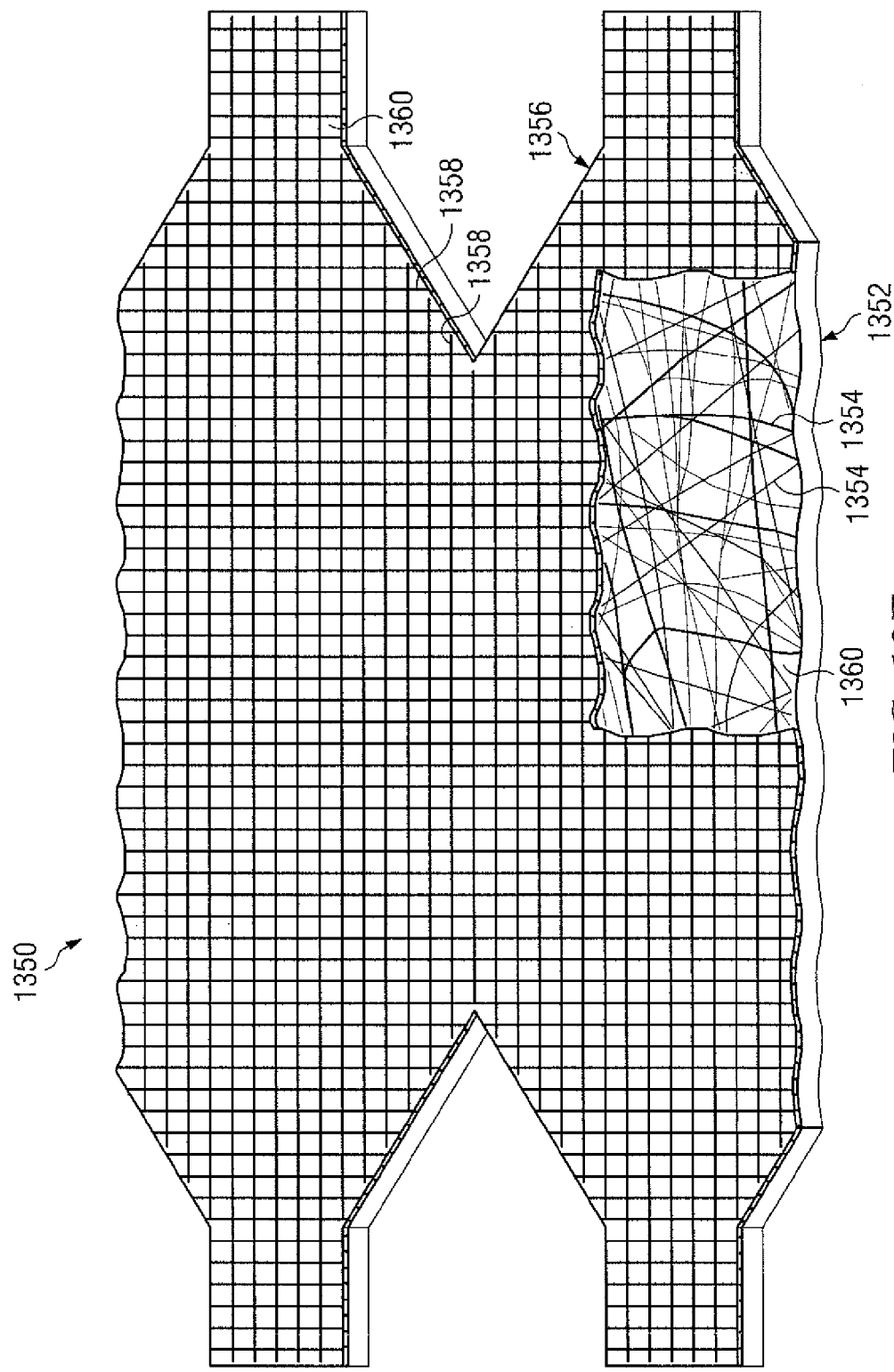

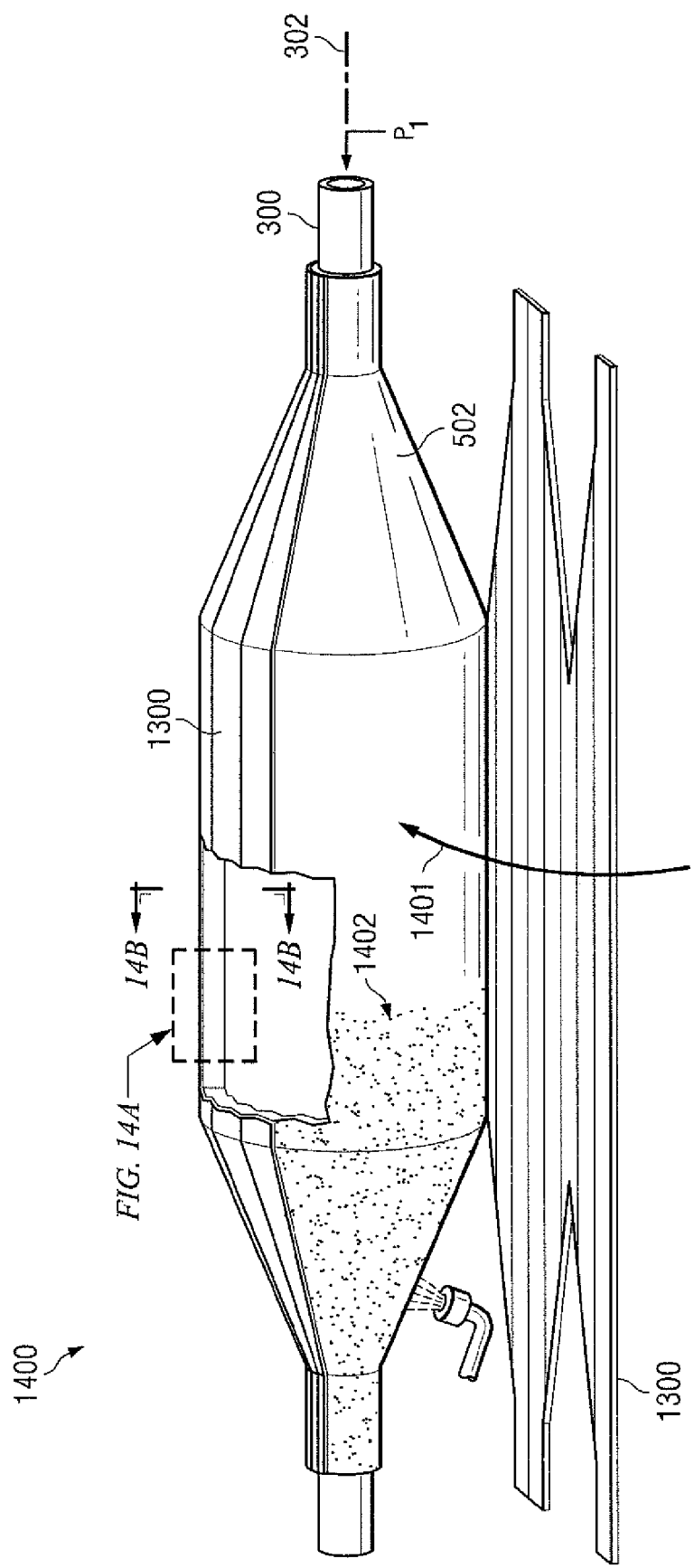

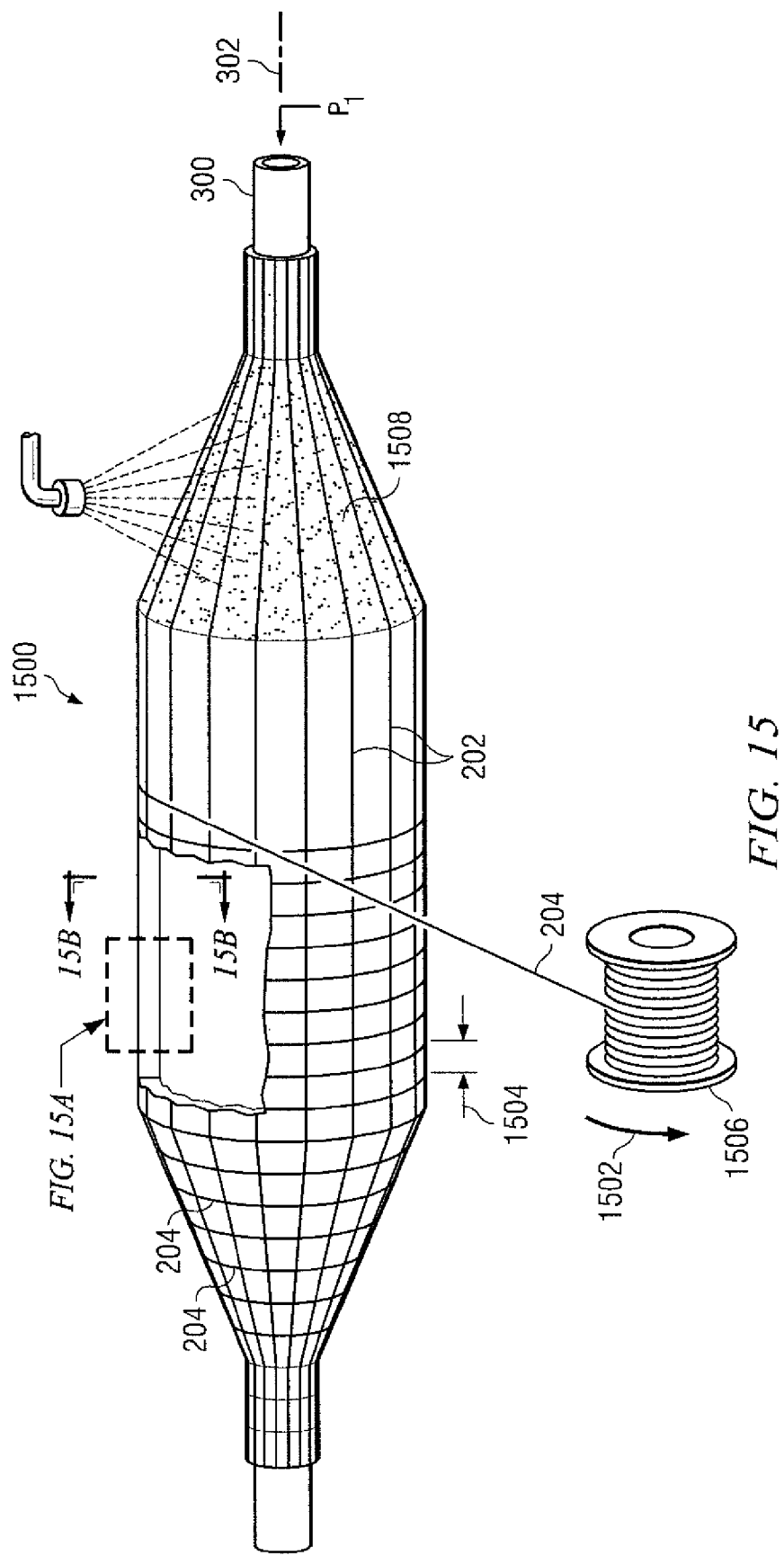

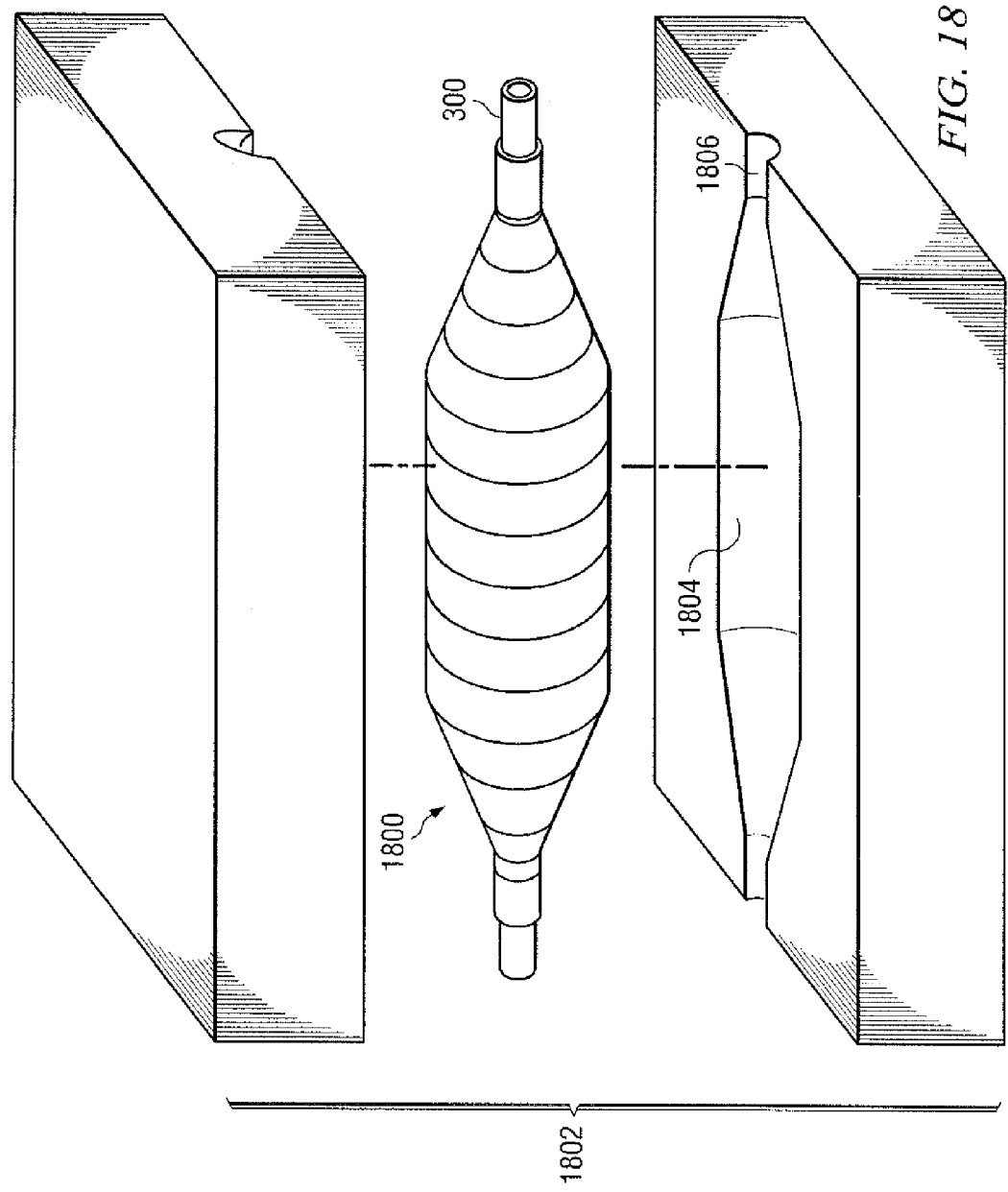

NON-COMPLIANT MEDICAL BALLOON

CROSS-REFERENCE TO RELATED APPLICATIONS

This application is a Continuation of U.S. patent application Ser. No. 12/537,850, filed on Aug. 7, 2007, which is a continuation of U.S. patent application Ser. No. 12/187,259, filed on Aug. 6, 2008 and entitled, "NON-COMPLIANT MEDICAL BALLOON," which claims priority to U.S. Provisional Application Ser. No. 60/954,252, filed on Aug. 6, 2007, and entitled "NON-COMPLIANT MEDICAL BALLOON," the specifications of which are incorporated herein by reference.

TECHNICAL FIELD

This disclosure relates to the field of medical balloons. In particular, it relates to non-compliant medical balloons that are useful in angioplasty and other medical applications including cardiology, radiology, urology and orthopedics.

BACKGROUND

Non-compliant medical balloons for performing angioplasty and other medical procedures are known. U.S. Pat. No. 6,746,425 to Beckham discloses a non-compliant medical balloon and methods for manufacturing the balloon. U.S. Patent Application Publication No. U.S. 2006/0085022 to Hayes et al. discloses a non-compliant medical balloon having an integral woven fabric layer and methods for manufacturing the balloon. U.S. Patent Application Publication No. U.S. 2006/0085023 to Davies, Jr. et al. discloses a medical balloon having strengthening rods and methods for manufacturing the balloon. U.S. Patent Application Publication No. U.S. 2006/0085024 to Pepper et al. discloses a non-compliant medical balloon having an integral non-woven fabric layer and methods for manufacturing the balloon. U.S. Pat. No. 6,746,425 and Publication Nos. U.S. 2006/0085022, US 2006/0085023 and U.S. 2006/0085024 are hereby incorporated herein by reference.

It is desirable to make the outer wall of a non-compliant medical balloon as thin as possible while still maintaining the required pressure rating or burst strength. In non-compliant balloons, the walls typically forms pleats when deflated (i.e., before or after inflation), and these pleats are folded over, wrapped and/or rolled around the long axis of the balloon. The thinner the wall material, the smaller the diameter of the deflated balloon. This smaller diameter facilitates passage of the deflated balloon through narrow vessels, lumens or cavities of the body prior to deployment. The walls of conventional non-compliant balloons include numerous discrete layers and/or components that tend to increase the thickness. A need therefore exists for a medical balloon having thinner walls and/or walls with fewer layers or components.

It is also desirable to make the outer wall of a non-compliant medical balloon as flexible as possible while still maintaining the required pressure rating or burst strength. The flexibility of the deflated balloon directly affects its "trackability," i.e., its ability to traverse sharp turns or branches of the vessels or body cavities through which the balloon must pass. The more flexible the walls, the better the trackability. The walls of conventional balloons often include physical adhesive layers needed to hold the disparate layers together or to prevent the movement of the wall components relative to one another. Unfortunately, the adhesives, e.g., polyurethanes, used are frequently stiffer than the materials/components being joined. Thus, these adhesive layers may undesirably increase the stiffness of the balloon walls. A need therefore exists for a medical balloon that eliminates or reduces the presence of adhesives in the finished balloon.

Conventional non-compliant balloons may have a wall thickness that varies considerably at different points of the balloon. For example, the wall thickness of the neck portion may be significantly thicker than the wall thickness of the barrel portion. Further, the wall thickness of the cone portion may vary from a relatively large thickness proximate the neck portion to a relatively low thickness proximate the barrel portion. This variation in wall thickness is frequently caused by the incorporation of blow-molded components (which have inherent wall thickness variability) into the structure of the balloon, but may be caused by other factors as well. Regardless of the cause, thicker walls in portions of the balloon that must be folded tend to affect adversely the user's ability to fold the deflated balloon into the desired diameter. This effect may be especially significant in the cone portion, where thicker cone walls can result in "bulges" at the front and the back of the folded balloon that are larger than the intervening barrel portion and, thus, force the user the increase the size of the introducer used to insert the balloon into the patient. It is thus desirable to develop non-compliant balloon construction methods yielding better control over the wall thickness of the balloon at all portions of the envelope. It is further desirable to make non-complaint medical balloons having relatively uniform wall thickness for the entire envelope, including the barrel, cone and neck portions.

It is still further desirable to simplify the construction of non-compliant medical balloons so as to reduce the amount of time and labor required for manufacture, to reduce the product defect rate, and/or to reduce the cost of production. The conventional construction of non-compliant balloons may require many discrete steps, some or all of which may require precision hand assembly that can be difficult or expensive to automate. A need therefore exists for improved methods of manufacturing non-compliant medical balloons.

SUMMARY

In one aspect thereof, there is disclosed a non-compliant fiber-reinforced medical balloon that may be inflated and deflated, and when inflated exhibits minimal change in radial distension across a predetermined range of internal pressures. The balloon has a generally cylindrical barrel wall disposed between tapered cone walls and cylindrical neck walls extending therefrom along a longitudinal axis. The balloon comprises a first fiber layer and a second fiber layer embedded in a continuous matrix of thermally-weldable polymer material defining a barrel wall, cone walls and neck walls. The fibers of the first fiber layer run substantially parallel to one another and substantially parallel to the longitudinal axis of the balloon. The fibers of the first fiber layer have a pattern of different lengths and are divisible into a first group and a second group based on length. Each fiber of the first group begins in the neck wall at one end of the balloon, extends continuously in the longitudinal direction and terminates in the neck wall at the opposite end of the balloon. Substantially all of the fibers of the first group have a generally uniform length. Each fiber of the second group begins in the cone wall at one end of the balloon, extends continuously in the longitudinal direction and terminates in the cone wall at the opposite end of the balloon. The length of the fibers of the second group varies progressively in accordance to their proximity to the fibers of the first group. The fibers of the second group closest to the fibers of the first group are longer than the fibers of the second group further from the fibers of the first group. The fiber of the second fiber layer winds circumferentially around the longitudinal axis of the balloon substantially over the entire length of the balloon including the neck walls, the cone walls and the barrel wall.

In another aspect thereof, there is disclosed a non-compliant medical balloon that may be inflated and deflated, and when inflated exhibits minimal change in radial distension across a predetermined range of internal pressures. The balloon has a generally cylindrical barrel wall disposed between tapered cone walls and cylindrical neck walls extending therefrom along a longitudinal axis. The balloon comprises an inner layer of thermally-weldable polymer material, a first fiber/polymer matrix layer disposed over the inner layer, a second fiber/polymer matrix layer disposed over the first fiber/polymer matrix layer, and an outer layer of thermally-weldable polymer material disposed over the second fiber/polymer matrix layer. The fibers of the first fiber/polymer matrix layer are substantially inelastic and run substantially parallel to one another and substantially parallel to the longitudinal axis of the balloon. The polymer of the first fiber/polymer matrix layer is a thermally-weldable polymer material. The fibers of the second fiber/polymer matrix layer are substantially inelastic and wind circumferentially around the longitudinal axis of the balloon substantially over the entire length of the balloon. The polymer of the second fiber/polymer matrix layer is a thermally-weldable polymer material. All of the thermally-weldable polymer materials from each of the layers have been fused together into a continuous polymer matrix encapsulating the fibers of the first and second fiber/polymer matrix layers and defining a barrel wall, cone walls and neck walls.

In another aspect, a method of making non-compliant fiber-reinforced medical balloon is disclosed. The method includes the steps of: (1) embedding a first fiber layer in a continuous matrix of thermally-weldable polymer, (2) cutting the first fiber layer in a pattern defining the generally cylindrical barrel wall, tapered cone walls and cylindrical neck walls wherein the fibers of the first fiber layer extend substantially parallel to the longitudinal axis of the balloon, and (3) wrapping the fiber of the second fiber layer circumferentially around the longitudinal axis of the balloon substantially over the entire length of the balloon including the neck walls, the cone walls and the barrel wall. In one embodiment, the fibers of the first fiber layer have a pattern of different lengths and are divisible into a first group and a second group based on length. The fibers of the first group begin in the neck wall at one end of the balloon, and extend continuously in the longitudinal direction and terminate in the neck wall at the opposite end of the balloon. The fiber of the second group begins in the cone wall at one end of the balloon and extends continuously in the longitudinal direction and terminating in the cone wall at the opposite end of the balloon. The length of the fibers of the second group vary progressively in accordance to their proximity to the fibers of the first group with the fibers of the second group closest to the fibers of the first group being longer than the fibers of the second group further from the fibers of the first group. In one variation, the first fiber layer is affixed over a mandrel before wrapping the fiber of the second fiber layer around the balloon. The method may further include embedding the second fiber layer in the continuous matrix of thermally-weldable polymer.

In yet another aspect, a non-compliant fiber-reinforced medical balloon that may be inflated and deflated, and when inflated exhibits minimal change in radial distension across a predetermined range of internal pressures includes a generally cylindrical barrel wall disposed between tapered cone walls and cylindrical neck walls extending therefrom along a longitudinal axis. The balloon includes a first textile layer comprising a plurality of substantially inelastic fibers embedded in a continuous matrix of thermally-weldable polymer material defining a barrel wall, cone walls and neck walls. The first textile layer may be one of a woven, knitted, braided or non-woven textile material. The balloon further includes a fiber layer wherein the fiber winds circumferentially around the longitudinal axis of the balloon substantially over the entire length of the balloon including the neck walls, the cone walls and the barrel wall, in one variation, the balloon includes an outer layer of thermally-weldable polymer material disposed over the second textile layer. The thermally-weldable polymer materials from each of the layers may be fused together into a continuous polymer matrix encapsulating the fibers of the first and second fiber/polymer matrix layers and defining the barrel wall, cone walls and neck walls.

BRIEF DESCRIPTION OF THE DRAWINGS

For a more complete understanding, reference is now made to the following description taken in conjunction with the accompanying Drawings in which:

FIG. 1 is a side view of a medical balloon in accordance with one embodiment;

FIG. 2 is a cross-sectional side view of the medical balloon of FIG. 1;

FIG. 3 a side view of a raw mandrel tube prior to blow-molding;

FIG. 4 shows the mandrel tube of FIG. 3 fitted with a polymer sleeve prior to blow-molding;

FIG. 5 shows the removable mandrel with conformal layer after blow-molding;

FIG. 13F shows a portion of a patterned sock including multiple textile reinforcement layers in accordance with another embodiment;

FIG. 14 illustrates affixing a patterned sock over the in-progress balloon and mandrel in accordance with additional embodiments;

FIG. 15 illustrates winding circumferential "hoop" reinforcing fibers around the in-progress balloon and mandrel in accordance with additional embodiments;

FIG. 18 illustrates placing the final balloon lay-up and mandrel into a die prior to thermal welding in accordance with additional embodiments;

DETAILED DESCRIPTION

Figure 2A:
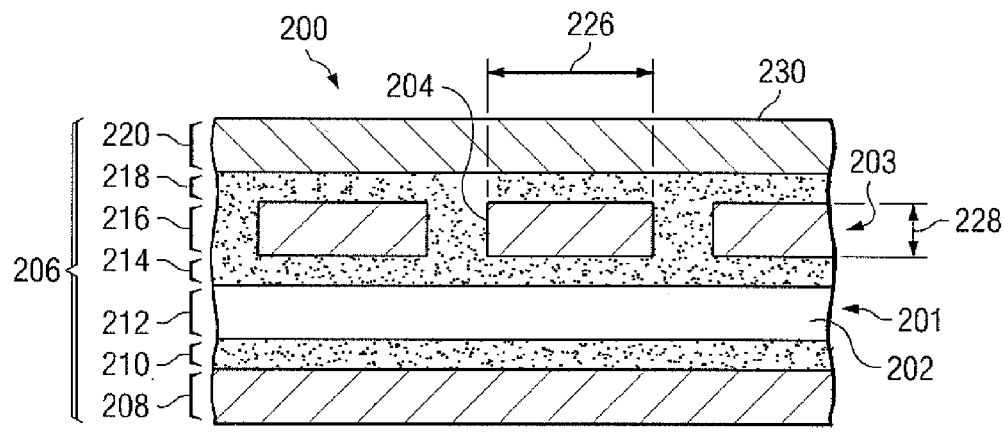
FIG. 2A is an enlarged cross-sectional view of the balloon wall looking in the circumferential direction taken along line 2A-2A of FIG. 2.

Referring now to the drawings, wherein like reference numbers are used herein to designate like elements throughout, the various views and embodiments of a non-compliant medical balloon are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a non-complaint medical balloon in accordance with one aspect, shown in its fully inflated state. Balloon 100 includes a generally cylindrical barrel portion 102 disposed between tapered cone portions 104 and cylindrical neck portions 106 extending therefrom along a longitudinal axis 108. The outer surface 110 of the cone portion 104 forms an angle 112 (the "cone angle") with respect to a longitudinal extension of the wall of the barrel portion 102. Conventional non-compliant balloons are typically limited to cone angles in the range of about 12 degrees to 16 degrees in order to minimize bulging (when folded) due to the thickness of the cone walls. As described further herein, embodiments of the balloon 100 may have a cone angle 112 in the range of 12 degrees to 22 degrees. In preferred embodiments, the cone angle 112 is in the range of 18 degrees to 22 degrees, and in more preferred embodiments, the cone angle 112 is about 20 degrees. The higher cone angle 112 results in shorter overall length for the balloon for a given barrel length.

Referring now to FIG. 2, a balloon 100 is shown in cross-section to illustrate further its structure. The diameter of the barrel portion 102 of the balloon ranges between a maximum size when inflated, denoted $D_1$, and a minimum size when deflated and folded, denoted $D_D$ (not shown). The diameter of the neck portion 106, denoted $D_N$, stays substantially constant regardless of inflation state. In preferred embodiments, the deflated diameter $D_D$ of the balloon is substantially equal to the neck diameter $D_N$. The barrel portion 102 of the balloon has a length, denoted $L_B$, measured between cone portions 104. The overall length, denoted $L_O$, is generally measured to the outer ends of the cone portions 104.

The walls of the balloon 100 include a barrel wall 114 having a relatively constant thickness, denoted $T_B$, cone walls 116 having a thickness ranging from a minimum, denoted $T_{CMIN}$, to a maximum, denoted $T_{CMAX}$, and neck walls 122 having a relatively constant thickness, denoted $T_N$. In prior art non-compliant balloons, $T_{CMIN}$ was often located near the barrel end 118 of the cone wall 116 and $T_{CMAX}$ was often located near the neck-end 120. In the improved balloons disclosed herein, $T_{CMIN}$ and $T_{CMAX}$ may be disposed at locations other than those shown, and in some embodiments the wall thickness along the cone wall 116 may be essentially constant such that $T_{CMIN}$ and $T_{CMAX}$ are approximately equal. In preferred embodiments, the cone walls 116 of balloon 100 have a relatively constant thickness such that the difference between $T_{CMAX}$ and $T_{CMIN}$ is not greater than $\pm 10\%$ of $T_{CMIN}$. More preferably, the difference between $T_{CMAX}$ and $T_{CMIN}$ is not greater than ±5% of $T_{CMIN}$. In still further embodiments, the thickness of the barrel wall 114 and cone walls 116 (collectively referred to as the "folding walls" since they must be folded when the balloon is in the deflated state to achieve the minimum diameter $D_D$) are substantially equal such that the difference between wall thicknesses $T_B$, $T_{CMIN}$ and $T_{CMAX}$ is not greater than ±10% of $T_B$. More preferably, the maximum difference between the folding wall thicknesses $T_B$, $T_{CMIN}$ and $T_{CMAX}$ is not greater than ±5% of $T_B$.

Figure 2B:
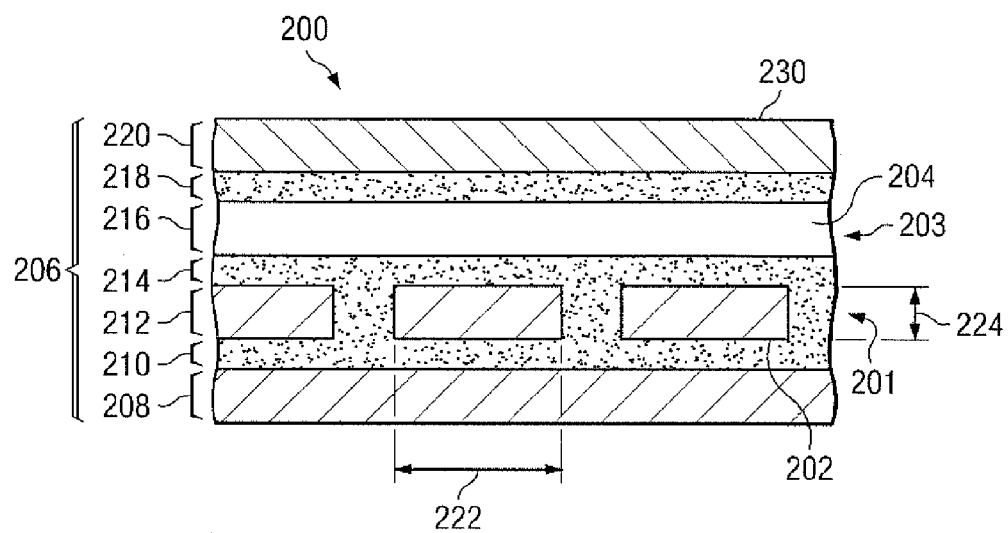
FIG. 2B is an enlarged cross-sectional view of the balloon wall looking in the longitudinal direction taken along line 2B-2B of FIG. 2.

Referring now to FIGS. 2A and 2B, enlarged cross-sections of the wall of balloon 100 are shown to illustrate the structure further. Although the illustrated cross-sections are taken through the barrel wall 114, as further disclosed herein the wall structures in the barrel wall 114, cone walls 116 and neck walls 122 are substantially identical to one another and will therefore collectively be identified as balloon wall 200. The balloon wall 200 has a composite structure including a first layer 201 of longitudinally-oriented reinforcing fibers 202 and second layer 203 of circumferentially- or "hoop-" oriented reinforcing fibers 204 embedded in a matrix 206 of thermally-weldable polymer material. The matrix 206 may be a single material or it may comprise multiple regions of compatible thermally-weldable polymer material that have been thermally welded into a continuous matrix. It will be appreciated that thermal welding, wherein heat and pressure alone are used to form a bond between the materials being joined, is differentiated from adhesive bonding, wherein an adhesive material (e.g., epoxy, polyurethane, etc.) is introduced between the materials being joined. In the illustrated embodiment, the matrix material 206 comprises an inner region 208, a first coating region 210, a sock region 212 (disposed primarily between the longitudinal fibers 202), a second coating region 214, a third coating region 216, a fourth coating region 218 and an outer region 220, all of which are compatible thermally-weldable materials. Preferably, the matrix 206 does not include any adhesive layers.

In one embodiment, the matrix 206 may be formed of thermally-weldable nylon (i.e., aliphatic polyamide) or polyamide blend. In another embodiment, the first coating region 210, the sock region 212, the second coating region 214, the third coating region 216 and the fourth coating region 218 are formed of soluble nylon and the inner region 208 and the outer region 220 are formed of a polyether block amide (PEBA), a nylon-containing thermoplastic blend, having a durometer hardness in the range from about Shore D 25 to about Shore D 54. Since both materials contain substantial parts nylon, they are thermal-welding compatible. In a preferred embodiment, the first coating region 210, the sock region 212, the second coating region 214, the third coating region 216 and the fourth coating region 218 are formed of soluble nylon and the inner region 208 and the outer region 220 are formed of Type-5533 PEBAX® brand PEBA having a durometer hardness of about Shore D 55.

It will be appreciated that the thickness of the fibers and regions in FIGS. 2A and 2B are not necessarily shown to scale. Also, some of the matrix regions may not be present in every portion of the balloon wall 200. For example, in some embodiments the second coating region 214 may be disposed only in the cone walls 116 portion of the balloon wall.

The longitudinally-oriented reinforcing fibers 202 are substantially inelastic fibers oriented parallel or substantially parallel to one another and parallel within ±10 degrees to the balloon's longitudinal axis 108. The circumferentially- or hoop-oriented reinforcing fibers 204 are substantially inelastic fibers oriented parallel or substantially parallel to one another and perpendicular within ±10 degrees to the longitudinally-oriented reinforcing fibers 202. The reinforcing fibers 202 and 204 may be formed of a variety of inelastic materials, including, but not limited to, Kevlar, Vectran, Spectra, Dacron, Dyneema, Turlon (PBT), Zylon (PBO), polyimide (PIM) and other ultrahigh molecular weight polyethylenes, aramids, and the like. In one embodiment, the longitudinal fibers 202 and the hoop fibers 204 may be aramid fibers, preferably multi-filament. In another embodiment, the longitudinal fibers 202 and the hoop fibers 204 may be para-aramid fibers, multi-filament. In a preferred embodiment, the longitudinal fibers 202 and the hoop fibers 204 may be Technora® brand paraphenylene/3,4-oxydiphenylene/terephthal amide copolymer, preferably multi-filament. The material of the reinforcing fibers 202 and 204 need not be thermally-weldable since the fibers are encapsulated in the matrix 206, however, the fiber material must be thermally compatible with the matrix material. In this context, the term "thermally compatible" is used to indicate that the material of the reinforcing fibers 202 and 204 can withstand the heat and temperatures required for thermal welding of the materials forming the matrix 206 without material degradation.

Referring still to FIGS. 2A and 2B, the longitudinal reinforcing fibers 202 have a width 222 and a thickness 224, and the hoop reinforcing fibers 204 have a width 226 and a thickness 228. Preferably, the reinforcing fibers 202 and 204 are "flattened" to reduce the overall thickness of the balloon wall 200 while maintaining the same cross-sectional area. In some embodiments, the longitudinal fibers 202 have a width-to-thickness ratio in the range from about 25:1 to about 45:1, and in preferred embodiments, the longitudinal fibers 202 have a width-to-thickness ratio in the range from about 30:1 to about 40:1. In some embodiments, the hoop fibers 204 have a width-to-thickness ratio in the range from about 25:1 to about 45:1, and in preferred embodiments, the hoop fibers 204 have a width-to-thickness ratio in the range from about 30:1 to about 40:1.

Although the balloon 100 may be constructed to any dimensions, balloons having a deflated diameter $D_D$ in the range from about 4 French Units (i.e., about 0.053 inches or 1.35 millimeters) to about 12 French Units (i.e., about 0.158 inches or 4.0 millimeters) are particularly useful in the fields of cardiology, radiology, orthopedics and urology. Producing such small diameter non-complaint balloons requires extremely thin balloon walls. In one embodiment, balloon 100 is a medical balloon having a deflated diameter $D_D$ in the range of 4 to 12 French Units and a folding wall thickness (i.e., $T_B$ and $T_{CMAX}$) in the range of about 0.001 inches to about 0.0023 inches (per wall). In another embodiment, balloon 100 is a medical balloon having a deflated diameter $D_D$ in the range of 4 to 12 French Units and a folding wall thickness in the range of about 0.0015 inches to about 0.0020 inches (per wall). In yet another embodiment, balloon 100 is a medical balloon having a deflated diameter $D_D$ in the range of 4 to 6 French Units and a folding wall thickness in the range of about 0.001 inches to about 0.0020 inches (per wall).

Referring now to FIGS. 3-22, details of the medical balloon 100 and methods for manufacturing such balloons are disclosed. In some embodiments, all of the longitudinal reinforcing fibers 202 may be attached to the balloon structure as part of a pre-formed sheet called a "sock." Use of this sock process may significantly simplify assembly of the balloon 100, reduce costs, improved quality and/or yield other benefits.

Referring first to FIG. 3, one method of construction of the balloon 100 begins with formation of a removable semi-compliant mandrel. The mandrel begins as a raw mandrel tube 300 comprising a tube of blow moldable material, such as polyethylene terephthalate (PET). The tube 300 has a longitudinal axis 302. For balloons in the 4 to 12 French Unit size, the raw mandrel tube 300 will typically have an outer diameter (O.D.) of about 0.05 inches to about 0.15 inches and a wall thickness of about 0.010 inches to about 0.020 inches.

Referring now to FIG. 4, an inner sleeve 400 of balloon matrix material is placed over the raw mandrel tube 300 prior to blow molding. The inner sleeve 400 will not become part of the removable mandrel; rather, it will become an integral part of the finished balloon, namely, the inner region 208 of the matrix 206. Accordingly, the materials of the raw mandrel tube 300 and of the inner sleeve 400 must be selected such that they do not thermally weld or otherwise stick together during subsequent operations as the balloon is constructed. For a mandrel formed of PET, the inner sleeve 400 may be formed of PEBA, such as Pebax®. For balloons in the 4 to 12 French Unit size, inner sleeve 400 may be formed of PEBA having a thickness of about 0.004 inches to about 0.005 inches per wall (before blow molding).

Figure 5A:
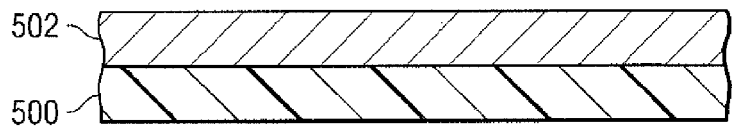
FIG. 5A is an enlarged cross-sectional view of the in-progress balloon wall overlying the mandrel looking in the circumferential direction taken along line 5A-5A of FIG. 5.
Figure 5B:
FIG. 5B is an enlarged cross-sectional view of the in-progress balloon wall overlying the mandrel looking in the longitudinal direction taken along line 5B-5B of FIG. 5.

Referring now to FIGS. 5, 5A and 5B, the raw mandrel tube 300 with the inner sleeve 400 in place is blow-molded using conventional techniques to form a balloon-shaped semi-compliant mandrel 500 covered by a conformal layer 502 of material from the sleeve 400. The longitudinal axis 302 of the raw mandrel tube 300 now becomes the longitudinal axis of the mandrel 500. The conformal layer 502 will ultimately become the inner region 208 of the balloon wall 200. As best seen in FIGS. 5A and 5B, the walls of the mandrel 500 and the conformal layer 502 are generally uniform when viewed in cross-section in either the circumferential or longitudinal direction. When constructing balloons 100 in the 4 to 12 French Unit size, the wall thickness of the mandrel 500 after blow-molding may be within the range of about 0.005 inches to about 0.0015 inches along the barrel, and the thickness (per wall) of the conformal layer 502 after blow-molding may be in the range of about 0.0003 inches to about 0.0006 inches. The shape of the mandrel 500 is maintained during the balloon-construction process by internally pressurizing the mandrel to a predetermined pressure.

Figure 6:
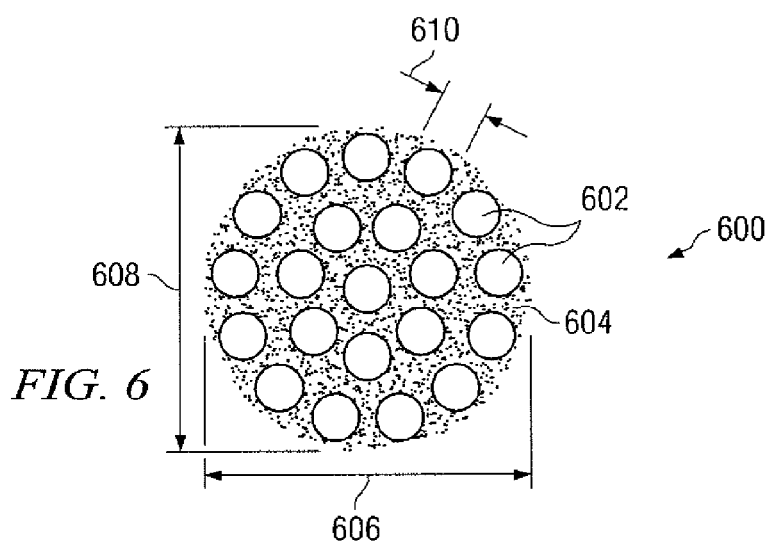
FIG. 6 is a cross-sectional end view of a tow of inelastic fiber material prior to flattening.

Referring now to FIG. 6, the inelastic fiber material used to make the reinforcing fibers 202 and 204 of balloon 100 may originally be provided in the form of a bundle or "tow" 600 of individual filaments 602. An adhesive or gel 604 may be included between the filaments 602 to help maintain the shape of the tow 600. The tow may have a generally circular cross-section with a width 606 and thickness 608 substantially equal to one another and substantially greater than the thickness 610 of an individual filament 602.

Figure 7:
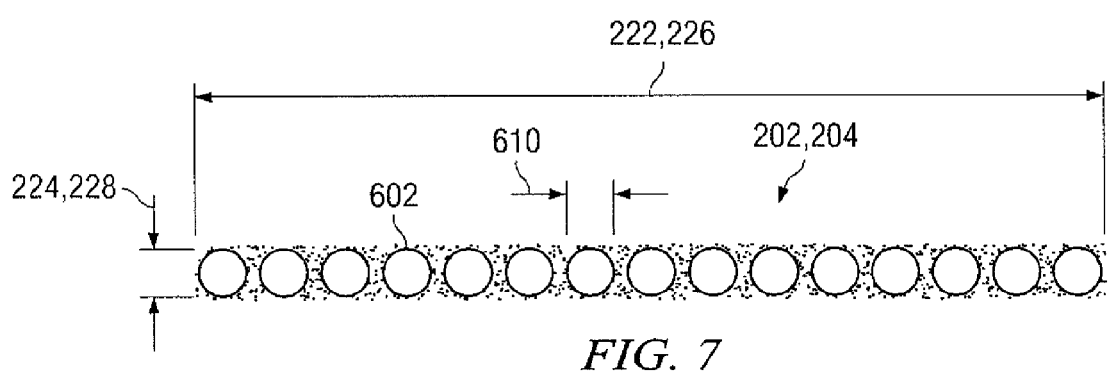
FIG. 7 is a cross-sectional end view of a flattened tow of inelastic fiber material used as a reinforcing fiber in some embodiments.

Referring now to FIG. 7, there is illustrated a tow of inelastic fiber material that has been modified to form reinforcing fibers 202, 204 having a flattened cross-section. In preferred embodiments, the thickness 224, 228 of the fibers 202, 204, respectively, may be within the range of about 1 to 2 times the thickness 610 of an individual filament 602. For example, Technora® brand para-aramid fiber having an original tow thickness 608 of about 0.003 inches and a filament thickness 610 of about 0.0005 inches may be flattened to form reinforcing fibers 202, 204 having a thickness 224, 228 of about 0.0005 inches and a width 222, 226 of about 0.015 inches.

Figure 8:
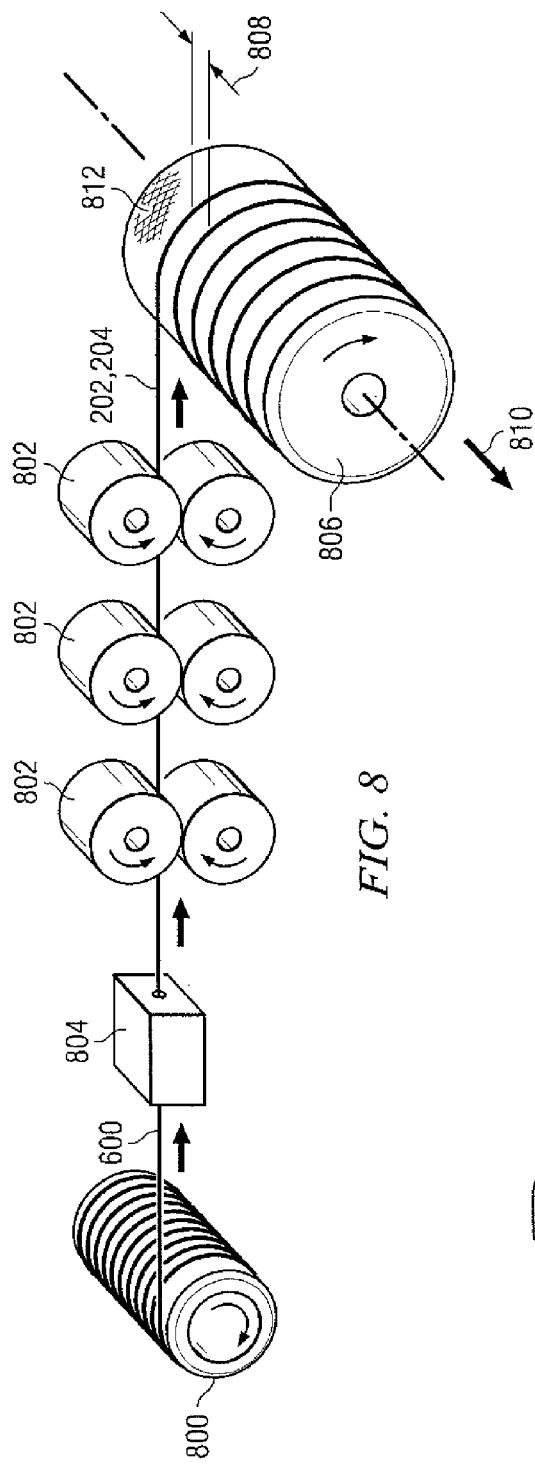
FIG. 8 illustrates forming flattened reinforcing fibers and preparing fiber-reinforced polymer sheets in accordance with additional embodiments.

Referring now to FIG. 8, one process for forming the flattened reinforcing fibers 202, 204 is illustrated. The original tow 600 of inelastic fiber is unreeled from a supply drum 800 and squeezed between one or more sets of closely spaced-apart rollers 802. A solvent or solvent-based adhesive may be applied to the tow 600 at a wetting-station 804 to remove or soften the original adhesive/gel 604 and facilitate rearrangement of the filaments 602 within the tow. The spacing between the final set of rollers 802 controls the thickness of the reinforcing fiber 202, 204. After leaving the final set of rollers 802, the fibers 202, 204 may be dried, if necessary, and then used immediately or stored for later processing.

Referring still to FIG. 8, one process for forming the so-called sock (i.e., the pre-formed sheet incorporating the longitudinal reinforcing fibers 202) begins by winding the flattened fiber 202 onto a sock drum 806 at a predetermined pitch (i.e., distance between successive fiber positions) 808. In the illustrated embodiment, the flattened fiber 202 is wound onto the sock drum 806 directly after leaving the flattening rollers 802, however, in other embodiments the fiber 202 may be processed earlier and provided from a storage roll (not shown). The pitch 808 between successive winds of fiber 202 may be produced by moving the sock drum 806 laterally (denoted by arrow 810) while winding or by moving the fiber feed laterally across the sock drum while winding. In some embodiments, the pitch 808 is selected to provide a spacing (i.e., spacing=pitch minus fiber width) between winds that is less than one fiber width 222. In preferred embodiments, the pitch 808 is selected to provide spacing between winds that is less than 50% of the fiber width 222, and in more preferred embodiments, the pitch is selected to provide spacing between winds that is less than 25% of the longitudinal fiber width. For example, in one embodiment having longitudinal fibers 202 with width 222 of about 0.015 inches, the pitch 808 is about 66 TPI (threads per inch), leaving a space of only about 0.0002 inches between fibers.

Prior to winding the longitudinal reinforcing fibers 202 onto the sock drum 806, a layer of anti-stick/protective material 812 may be applied to the drum surface. In one embodiment, the anti-stick/protective materials 812 is a layer of Teflon® brand tape wrapped around the drum 806. The anti-stick/protective material 812 protects the fibers 202 from the drum and facilitates release of the sock from the drum after processing.

Figure 9:
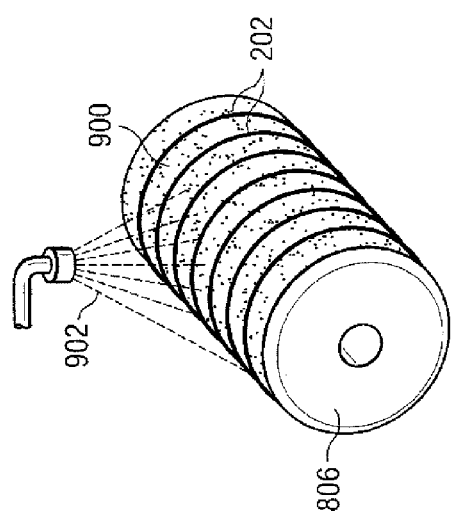
FIG. 9 illustrates coating the reinforcing fibers with polymer material during preparation of fiber-reinforced polymer sheets in accordance with additional embodiments.

Referring now to FIG. 9, after winding the reinforcing fibers 202 onto the drum 806, a sock coating 900 of thermally-weldable polymer material 902 may be applied across the fibers and surface of the drum. The sock coating 900 is preferably applied by spraying, but may be applied by brushing, dipping or other means. The sock coating 900 will ultimately become the sock region 212 of the matrix 206; therefore, it must be compatible for thermal-welding to the other materials in the matrix. In one embodiment, the sock coating 900 may be formed of a soluble nylon material having a thickness of about 0.0003 inches. In an alternative embodiment (not shown) the sock coating 900 is applied directly to the surface of the sock drum 806 (or, if present, to the anti-stick/protective material 812) before winding on the reinforcing fibers 202. In one such alternative embodiment, the sock coating 900 may be formed of a soluble nylon material having a thickness of about 0.0003 inches.

Figure 10:
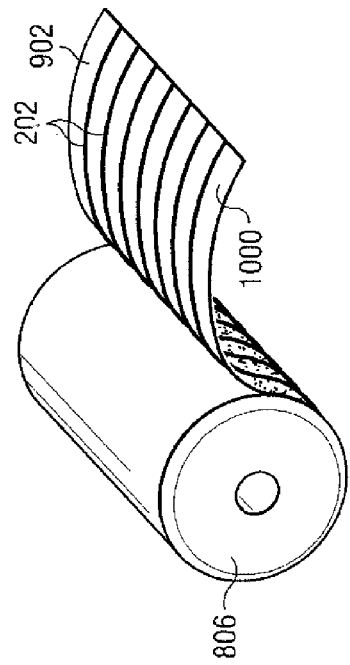
FIG. 10 illustrates removing sheets of polymer embedded with reinforcing fibers during preparation of fiber-reinforced polymer sheets in accordance with additional embodiments.

Referring now to FIG. 10, after applying the sock coating 900 to the longitudinal fibers 202 (or vice-versa) and allowing it to dry, the resulting sock sheet 1000 is cut and removed from the drum 806. The sock sheet 1000 now comprises a plurality of substantially parallel reinforcing fibers 202 affixed to a film of thermally-weldable polymer material 902 (from the sock coating 900).

Figure 11:
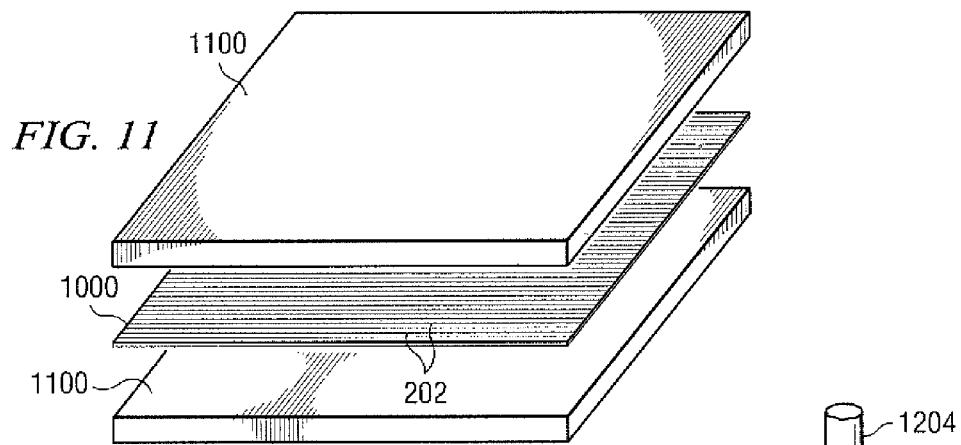
FIG. 11 illustrates fusing and flattening fiber-reinforced polymer sheets in accordance with additional embodiments.

Referring now to FIG. 11, the sock sheet 1000 is pressed and heated to smooth its surfaces and firmly embed the reinforcing fibers 202 into the thermally-weldable matrix material 902. In one embodiment, the sock sheet 1000 is placed between two flat steel sheets 1100, clamped together, and heated in an oven (not shown). In another embodiment, wherein the reinforcing fibers 202 are Technora® brand para-aramid fibers approximately 0.0005 inches thick, and the thermally-weldable material 902 is nylon, the sock sheet is heated between flat steel sheets at 250 degrees F. for a period within the range of about 20 to 30 minutes. During the pressing/heating procedure, the matrix material 902 may plastically deform such that, after cooling, the sheet is perfectly smooth and has the thickness of the reinforcing fibers 202.

Referring now to FIGS. 12, 13, and 13A-F, the finished sock sheet 1000 is next patterned and cut to shape. A flat pattern 1200 may be created corresponding to the outer wall of the balloon 100, wherein the pattern represents the three-dimensional outer surface of the balloon that has been cut along lines parallel to the longitudinal axis 108 and "unfolded" into a two-dimensional (i.e., flat) surface. The pattern 1200 will have a pattern axis 1202 corresponding to a line on the surface of the balloon 100 that is parallel to the longitudinal axis 108. In the illustrated embodiment, the pattern 1200 may correspond to the entire outer wall of the balloon 100 (including the barrel wall 114, cone walls 116 and neck walls 122). In another embodiment, the pattern 1200 may correspond to selected portions of the outer wall of the balloon 100. In preferred embodiments, the pattern 1200 will correspond to portions of the surface of the balloon extending longitudinally along the entire length of the balloon, i.e., from the outer end of one neck to the outer end of the opposite neck.

Figure 12:
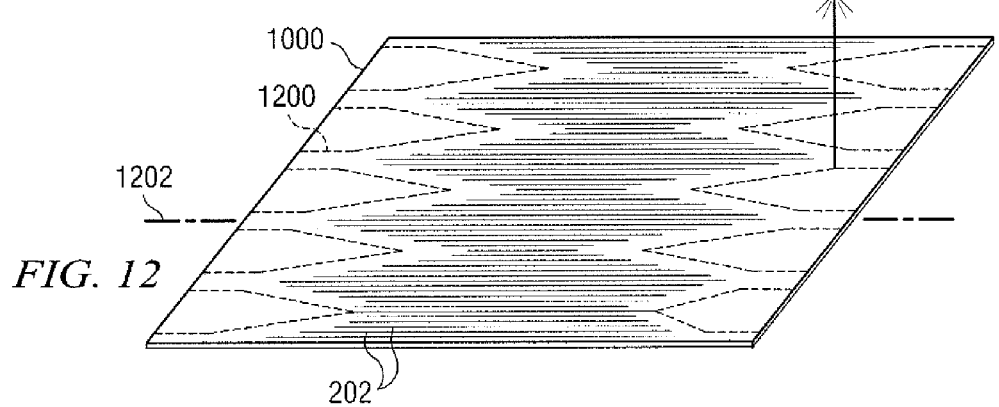
FIG. 12 illustrates patterning and cutting a pre-fabricated fiber-reinforced balloon wall layer (also called a "sock") in accordance with additional embodiments.

Referring now specifically to FIG. 12, for purposes of illustration the reinforcing fibers 202 may be shown in FIG. 12 as having an abbreviated length in order to more clearly show the pattern 1200, however it will be understood that the fibers 202 may actually run across the entire length of the sock sheet 1000 as shown in FIG. 11. The pattern 1200 may be superimposed on the sock sheet 1000 with the pattern axis 1202 oriented substantially parallel to the reinforcing fibers 202. This may ensure that the longitudinal reinforcing fibers 202 run substantially parallel to the longitudinal axis 108 in the finished balloon 100. The pattern 1200 may then be cut out of the sock sheet 1000 to form the final patterned sock 1300. In one embodiment, the pattern 1200 may be transferred to the surface of the sock sheet 1000 (e.g., by printing) and the patterned sock 1300 may be cut out by hand (e.g., by knife, scissors, etc.). In another embodiment, the pattern 1200 may be incorporated into the shape of a cutting tool (e.g., a cutting die or cutting punch) and the patterned sock 1300 may be cut from the properly oriented sock sheet 1000 by an automated cutting apparatus (e.g., a die cutting machine) using the cutting tool. In yet another embodiment, the pattern 1200 may be incorporated into a computer program or set of CNC instructions and the patterned sock 1300 may be cut from the properly oriented sock sheet 1000 by a computer-controlled/CNC cutting apparatus, e.g., a laser cutter 1204 (shown in FIG. 12), a water jet cutter or numerically-controlled knife.

Figure 13:
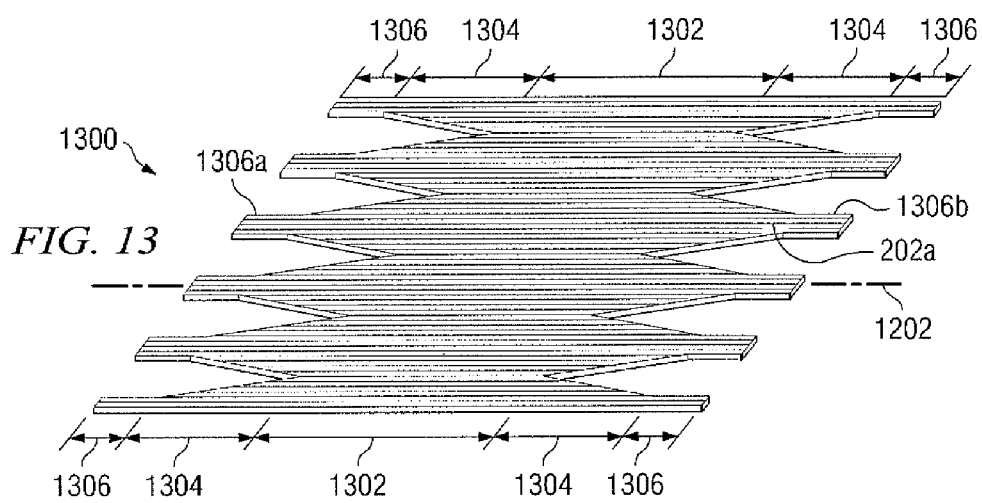
FIG. 13 shows a perspective view of a patterned sock, i.e., a prefabricated fiber-reinforced balloon wall layer, in accordance with additional embodiments.

Referring now specifically to FIG. 13, the finished patterned sock 1300 may include barrel, cone and neck portions 1302, 1304 and 1306, respectively corresponding to the barrel, cone and neck portions 102, 104 and 106 of the finished balloon 100. In the finished patterned sock 1300, selected reinforcing fibers 202 may extend continuously from one longitudinal end of the patterned sock to the opposite longitudinal end. For example, in the embodiment illustrated in FIG. 13, reinforcing fiber 202*a* extends continuously from neck portion 1306*a* at one longitudinal end of the patterned sock to neck portion 1306*b* at the opposite longitudinal end.

Figure 13A:
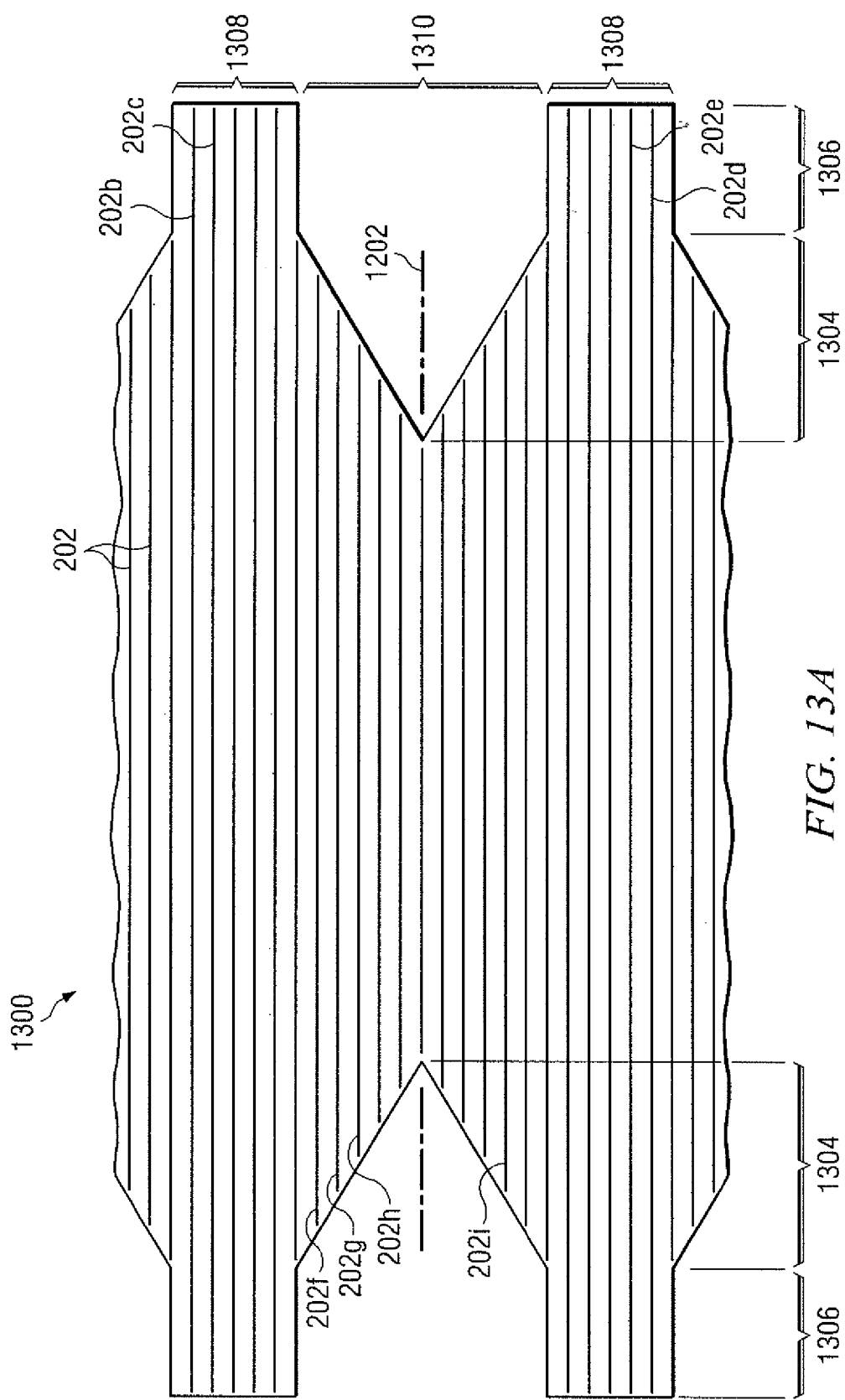
FIG. 13A shows an enlarged view of a portion of the patterned sock of FIG. 13 to better illustrate the pattern of the reinforcing fibers.

Referring now specifically to FIG. 13A, an enlarged portion of the patterned sock 1300 is shown to better illustrate the pattern of the reinforcing fibers 202 within the sock. It will be understood that outline of the sock shown in FIG. 13A is for purposes of illustration and is not intended to show the exact shape necessary to cover the balloon shown in FIG. 1. As previously described, the fibers 202 of the patterned sock 1300 may run substantially parallel to one another and substantially parallel to the sock axis 1202 that may be aligned with the longitudinal axis 108 of the balloon. The fibers 202 in the sock may have a pattern of different lengths such that the fibers may be divided into a first group and a second group based on length. The first group may be termed the "neck group" (denoted by reference number 1308 in FIG. 13A) and the second group may be termed the "cone group" (denoted by reference number 1310).

Each fiber of the neck group 1308 begins in the neck wall portion 1306 at one end of the sock, extends continuously in the longitudinal direction and terminates in the neck wall portion at the opposite end of the sock. The fibers denoted 202*b*, 202*c*, 202*d* and 202*e* are examples of fibers in the neck group 1308. Substantially all of the fibers 202 in the neck group 1308 have a generally uniform length.

Each fiber of the cone group 1310 begins in the cone wall portion 1304 at one end of the sock, extends continuously in the longitudinal direction and terminates in the cone wall portion at the opposite end of the sock. The fibers denoted 202*f*, 202*g*, 202*h* and 202*i* are examples of fibers in the cone group 1310. In contrast to the previous group, the length of the fibers 202 of the cone group 1310 varies progressively in accordance to their proximity to the fibers of the neck group 1308. The fibers of the cone group closer to the fibers of the neck group are longer than the fibers of the cone group further from the fibers of the neck group. Accordingly, fiber 202*f*, which is closest to the neck group 1308, is the longest of the example fibers, while fiber 202*h*, which is farthest from the neck group, is the shortest of the example fibers. Fiber 202*g*, disposed between fibers 202*f* and 202*h*, has an intermediate length. Fiber 202*i* has a length approximately equal to that of fiber 202*g*, because each is approximately the same distance from a neck group 1308.

Figures 13B, 13C, 13D, 13E:
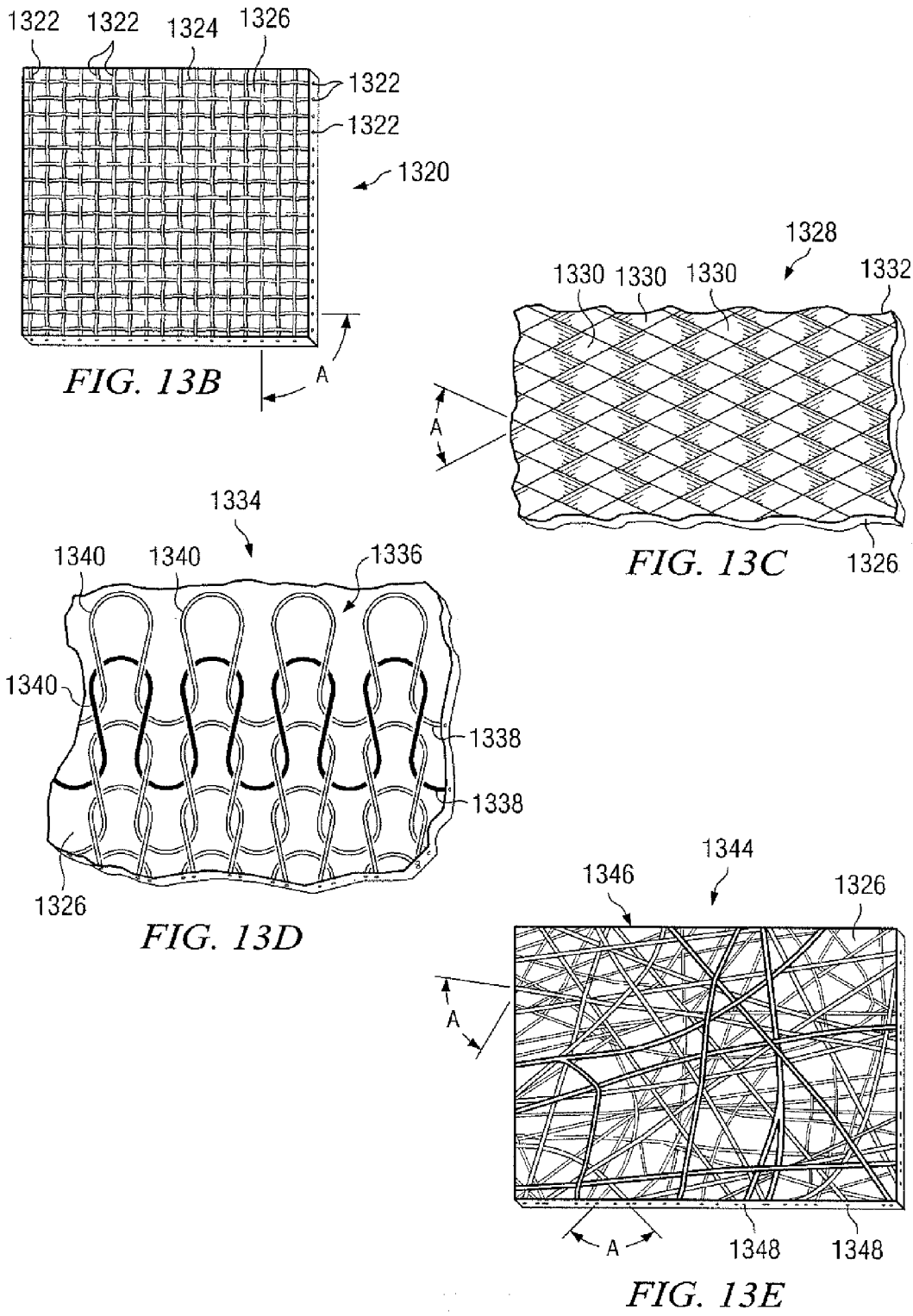
FIG. 13B shows an enlarged view of a portion of sock sheet similar to the sock of FIG. 13, but incorporating woven textile reinforcement in accordance with an alternate embodiment.
FIG. 13C shows an enlarged view of a portion of sock sheet similar to the sock of FIG. 13, but incorporating braided textile reinforcement in accordance with an alternate embodiment.
FIG. 13D shows an enlarged view of a portion of sock sheet similar to the sock of FIG. 13, but incorporating knitted textile reinforcement in accordance with an alternate embodiment.
FIG. 13E shows an enlarged view of a portion of sock sheet similar to the sock of FIG. 13, but incorporating non-woven textile reinforcement in accordance with an alternate embodiment.

Turning to FIG. 13B, in an alternative embodiment, a sock sheet 1320 may be reinforced by weaving fibers 1322 into a woven textile material 1324. The woven textile material 1324 has a structure wherein fibers or filaments are interlaced. Fibers 1322 may be flattened prior to weaving as described above, or the woven textile material 1324 may be pressed, for example between rollers to achieve the desired thickness. In this variation, woven textile material 1324 may be coated with a thermally-weldable polymer material 1326, as described in connection with FIG. 9. After the coating has been applied, the sock sheet 1320 may be clamped between plates and heated to embed the fibers 1322 within the thermally-weldable polymer 1326 and produce a sheet 1320 having smooth surfaces. Alternatively, a film formed from a thermally-weldable polymer material may be placed over woven textile material 1324 prior to heating to form a sock sheet 1320. Fibers 1322 may form angles (denoted "A") at the intersections thereof that remain constant when a balloon incorporating sock material 1320 is inflated and deflated.

After embedding, the finished sock sheet 1320 formed using woven textile material 1324 may then be patterned and cut to shape as described above. For purposes of illustration, the weave of textile material 1324 is shown with a high porosity, i.e., a relatively large amount of open space between fibers 1322. Other woven textile fabrics having greater or lesser porosities, including those having a very tight weave with essentially no porosity may be used in other embodiments.

FIG. 13C illustrates another alternative embodiment, wherein a reinforced sock sheet 1328 may be reinforced by braiding fibers 1330 into a braided textile fabric 1332. A braided fabric 1332 employs a fiber architecture in which three or more fibers are intertwined in such a way that no two fibers are twisted exclusively around one another. Since all of the fibers 1332 within a braided structure are continuous and mechanically locked, a braid has a natural mechanism that evenly distributes load throughout the structure. Braided textile fabric 1332 is formed from fibers 1330 that may be flattened before braiding. Alternatively, braided textile material 1332 may be otherwise processed to achieve the desired thickness. Braided textile material 1332 may be coated with a thermally-weldable polymer material 1326 and heated as described above to embed fibers 1330 within the thermally-weldable polymer to produce a sock sheet 1328 having uniform smooth surfaces. Alternatively, a film formed from a thermally-weldable polymer material 1326 may be placed over braided textile material 1332 prior to heating to form a sock sheet 1328. The finished sock sheet 1328 may then be patterned and cut to shape. After fibers 1330 have been embedded in the thermally-weldable polymer 1326, the angles (denoted "A") between the fibers preferentially remain constant when a balloon incorporating sock sheet 1328 is inflated and deflated.

FIGS. 13D and 13E illustrate additional embodiments, wherein reinforced sock sheets 1334 and 1344 are reinforced by knitted textile material 1336 and non-woven textile material 1346, respectively. A knitted textile fabric is produced by intertwining fibers 1338 in a series of interconnected loops 1340 rather than by weaving. In this fashion, the loops 1340 of fibers 1338 are mechanically interlocked. A weft-knitted structure consists of horizontal, parallel courses of fibers and requires only a single fiber 1338. Alternatively, warp knitting requires one fiber 1338 for every stitch in the course, or horizontal row; these fibers make vertical parallel wales. In contrast, non-woven textile fabrics 1346 are typically made from randomly-oriented fibers that are neither woven nor knitted. The fibers 1348 in non-woven fabrics typically have a web structure in which small fibers or filaments are held together by inter-fiber friction (e.g., matting), thermal binding (e.g., with a meltable binder) or chemical adhesion.

Knitted textile material 1336 or non-woven textile material 1346 may be embedded in a thermally-weldable polymer 1326 as described above, cut and patterned to form a patterned sock material 1334 or 1344 similar to that shown in FIG. 13. In the case of the non-woven textile fabric 1346, the fibers 1348 may be randomly oriented, chopped fibers of the same or varying lengths that form random angles (denoted "A") at each fiber intersection. After the knitted fiber loops 1340 or non-woven fibers 1348 are embedded in the thermally-weldable polymer 1326, the relative positions of the loops 1340 or angles A between fibers preferably remains constant when a balloon incorporating sock sheet 1334 or 1344 is inflated and deflated.

The textile fabrics illustrated in FIGS. 13B-13E may be formed from a variety of substantially inelastic polymers. For example, Kevlar, Vectran, Spectra, Dacron, Dyneema, Turlon (PBT), Zylon (PBC)), polyimide (PIM) and other ultrahigh molecular weight polyethylenes, aramids, and similar polymers may be used to manufacture the fibers.

Referring now to FIG. 13F, in another variation, multiple textile reinforcing layers may be used to form a patterned sock 1350. In the illustrated embodiment, patterned sock 1350 is formed from a first non-woven textile layer 1352 having randomly oriented fibers 1354 and a second textile layer 1356 formed from woven fibers 1358. For purposes of illustration, portions of the sock 1350 are broken away in FIG. 13F to show both reinforcing layers 1352 and 1356. One or both of textile layers 1352 and 1356 may be coated with a thermally-weldable polymer material 1360, or pressed together and heated to embed fibers 1354 and 1358 in a continuous polymer matrix. In other embodiments, layers of knitted, braided, woven, non-woven and patterned fabrics textiles and fibers may be combined to form patterned sock sheets.

Figure 14A:
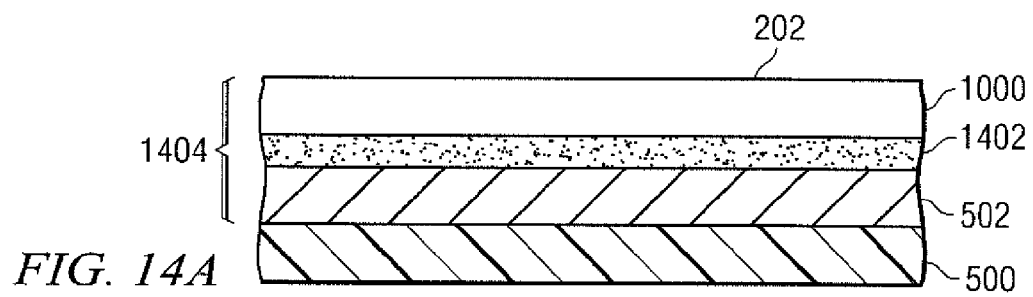
FIG. 14A is an enlarged cross-sectional view of the in-progress balloon wall overlying the mandrel looking in the circumferential direction taken along line 14A-14A of FIG. 14.
Figure 14B:
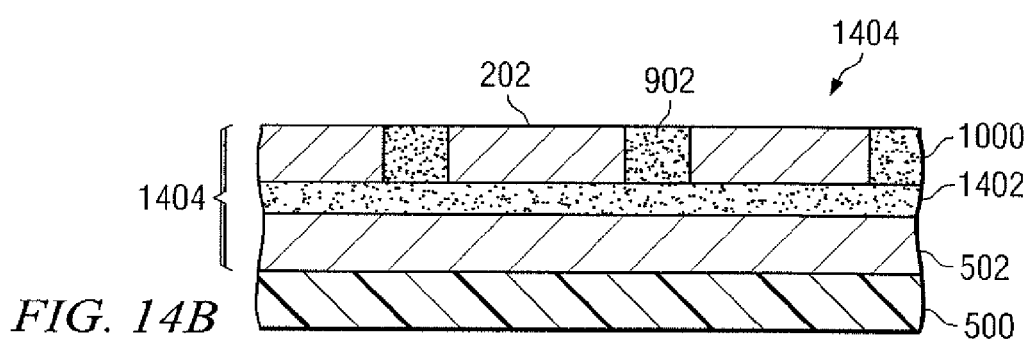
FIG. 14B is an enlarged cross-sectional view of the in-progress balloon wall overlying the mandrel looking in the longitudinal direction taken along line 14B-14B of FIG. 14.

Referring now to FIG. 14, 14A and 14B, the patterned sock 1300 (or alternatively, socks 1320, 1328, 1334, 1344 or 1350) may be affixed over the illustrated balloon lay-up 1400, which now comprises the conformal layer 502 covering the removable semi-compliant mandrel 500 (as seen in FIG. 5). The size and shape of the mandrel 500 is preserved during processing by maintaining a predetermined internal pressure $P_1$ via the tube 300. The patterned sock 1300 may be oriented such that the reinforcing fibers 202 are oriented parallel or substantially parallel to the longitudinal axis 302 of the mandrel 500 (which corresponds at this point to the longitudinal axis 108 of the final balloon 100). In some embodiments, the reinforcing fibers 202 are oriented within ±10 degrees of parallel to the longitudinal axis 302. In some embodiments, a one-piece patterned sock 1300 may be "rolled" (denoted by arrow 1401) onto the conformal layer 502 so as to cover the entire surface. Preferably, no adhesive materials are used to affix the patterned sock 1300 to the conformal layer 502.

The patterned sock 1300 will ultimately become the first layer 201 of longitudinally-oriented reinforcing fibers in the finished balloon 100. Embodiments in which the fibers 202 in the sock 1300 have a particular pattern may have a substantially similar pattern in the fibers of the first fiber layer 201 in the finished balloon 100. Embodiments in which the fibers 202 in the sock 1300 have a pattern of different lengths such that the fibers may be divided into a first group and a second group based on length may have a substantially similar pattern in the fibers of the first fiber layer 201 in the finished balloon 100. The thermally-weldable material in the sock sheet will become the sock region 212 of the matrix 206.

To facilitate attachment of the patterned sock 1300 to the conformal layer 502, in some embodiments a solvent compatible with the thermally-weldable material 902 of the sock sheet may be applied to "tackify" (i.e., to make slightly sticky or tacky) the inside surface of the patterned sock 1300. In other embodiments, a first coating 1402 of thermally-weldable material may be applied over the conformal layer 502 prior to affixing the patterned sock 1300. The first coating 1402 (if present) is preferably applied by spraying, but may be applied by brushing, dipping or other means. The first coating 1402 will ultimately become the first coating region 210 of the matrix 206, therefore it must be compatible for thermal-welding to the other materials in the matrix. In one embodiment the first coating 1402 may be formed of a soluble nylon material having a thickness of about 0.0003 inches. Such a first coating 1402 may be thermal-welding compatible with a conformal layer 502 when formed of PEBA such as Pebax®. It will be appreciated that the patterned sock 1300 may not be welded or permanently joined to the conformal layer 502 (or first coating 1402) at this time. It is only necessary that the patterned sock 1300 be affixed well enough to stay in position during further processing.

Referring now specifically to FIGS. 14A and 14B, after affixing the patterned sock 1300 over the conformal layer 502, the in-progress wall 1404 of the balloon 100 is illustrated on the outer surface of the mandrel 500. In the embodiment illustrated, the first coating 1402 has been applied as previously described.

Figure 15A:
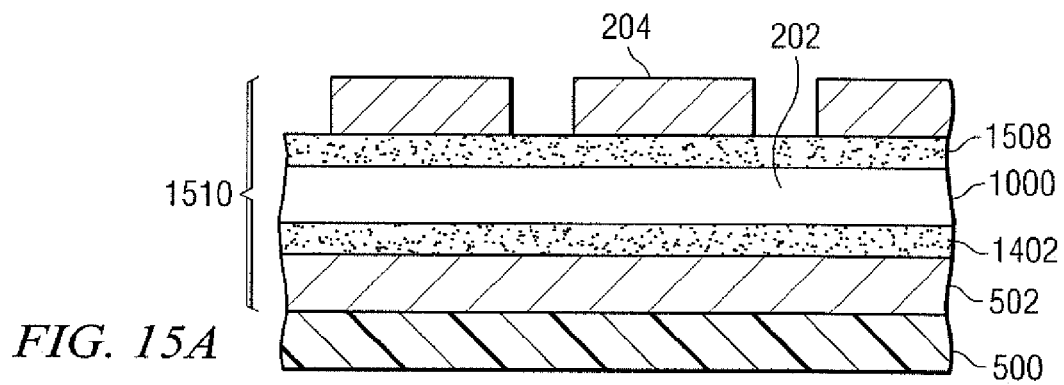
FIG. 15A is an enlarged cross-sectional view of the in-progress balloon wall overlying the mandrel looking in the circumferential direction taken along line 15A-15A of FIG. 15.
Figure 15B:
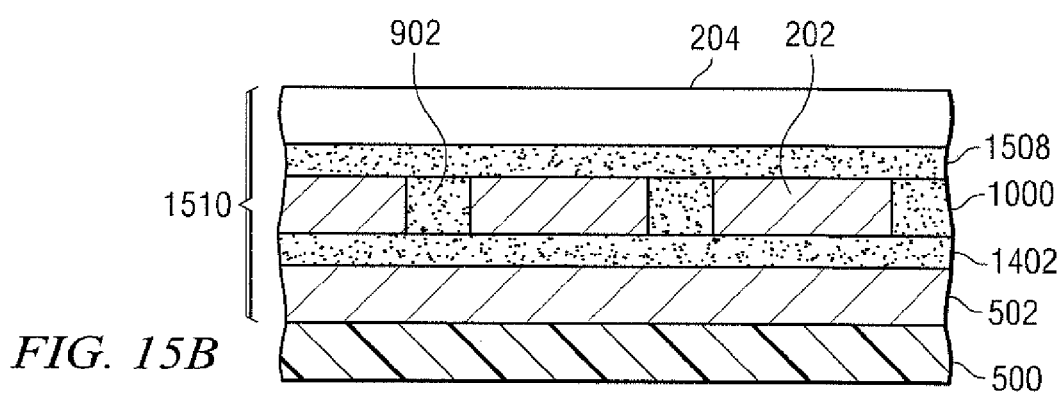
FIG. 15B is an enlarged cross-sectional view of the in-progress balloon wall overlying the mandrel looking in the longitudinal direction taken along line 15B-15B of FIG. 15.

Referring now to FIG. 15, 15A and 15B, the hoop reinforcing fibers 204 may be affixed over the illustrated balloon lay-up 1500, which now includes the patterned sock 1300 with longitudinal reinforcing fibers 202. The balloon lay-up 1500 is supported by the underlying mandrel 500, which remains pressurized at the predetermined internal pressure $P_1$ to maintain its size and shape. The flattened hoop reinforcing fibers 204 may be wound circumferentially around the balloon lay-up 1500 at a predetermined pitch 1504 such that successive winds are oriented parallel or substantially parallel to one another and perpendicular or substantially perpendicular to the longitudinally-oriented reinforcing fibers 202. In some embodiments, the hoop fibers 204 are wound within ±10 degrees of perpendicular to the longitudinal reinforcing fibers 202

The flattened hoop fibers 204 may be supplied from a storage drum 1506 or other source. In preferred embodiments, the fibers 204 may be wound continuously around the balloon lay-up 1500 from one neck to the opposite neck. In the illustrated embodiment, the circumferential winding (denoted by arrow 1502) is accomplished by revolving the storage drum 1506 around the balloon lay-up 1500, however in other embodiments the balloon lay-up and mandrel 500 may be rotated. In some embodiments, the hoop pitch 1504 is selected to provide a spacing between hoop winds that is less than one hoop fiber width 226. In preferred embodiments, the pitch 1504 is selected to provide spacing between hoop winds that is less than 50% of the hoop fiber width 226, and in more preferred embodiments, the pitch is selected to provide spacing between hoop winds that is less than 25% of the hoop fiber width. For example, in one embodiment having hoop fibers 204 with width 226 of about 0.015 inches, the pitch 1504 is about 66 TPI (threads per inch), leaving a space of only about 0.0002 inches between hoop fibers.

Prior to winding the hoop reinforcing fibers 204 onto the balloon lay-up 1500, a second coating 1508 of thermally-weldable matrix material may be applied to the surface of the balloon lay-up to facilitate retention of the hoop fibers. In some embodiments, the second coating 1508 is applied only to the surface of the cone portions 104, since the tendency for the fibers 204 to slip is greatest on the angled surfaces of the cones. The second coating 1508 (if present) is preferably applied by spraying, but may be applied by brushing, dipping or other means. The second coating 1508 will ultimately become the second coating region 214 of the matrix 206, therefore it must be compatible for thermal-welding to the other materials in the matrix. In one embodiment, the second coating 1508 may be formed of a soluble nylon material having a thickness of about 0.0003 inches. Such a second coating 1508 may be thermal-welding compatible with the first coating 1402 when formed of soluble nylon and/or the conformal layer 502 when formed of PEBA such as Pebak®. It will be appreciated that the patterned sock hoop fibers 204 may not be welded or permanently joined to the balloon lay-up at this time. It is only necessary that the hoop fibers 204 be affixed firmly enough to stay in position during further processing.

Referring now specifically to FIGS. 15A and 15B, after affixing the hoop reinforcing fibers, the in-progress wall 1510 of the balloon 100 is illustrated on the outer surface of the mandrel 500. In the embodiment illustrated, the second coating 1508 has been applied as previously described.

Figure 16:
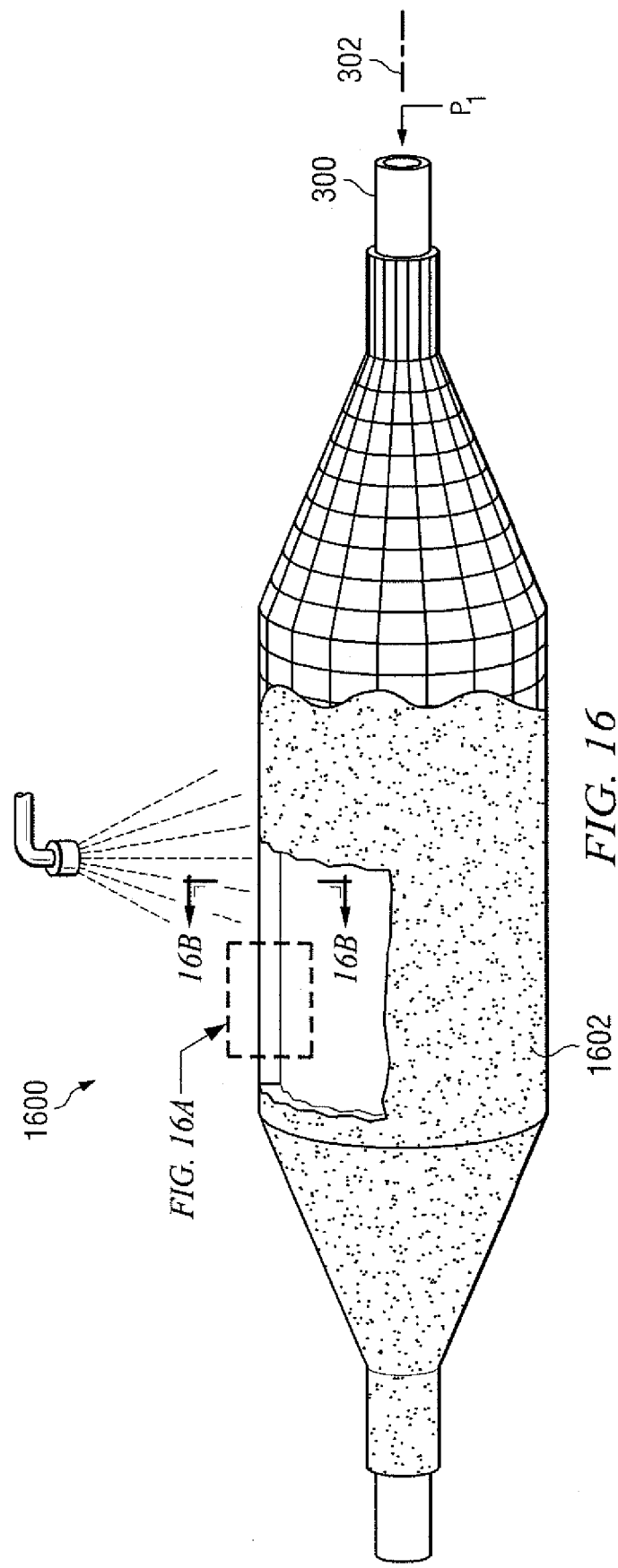
FIG. 16 illustrates applying a third coating layer over the in-progress balloon and mandrel in accordance with additional embodiments.
Figure 16A:
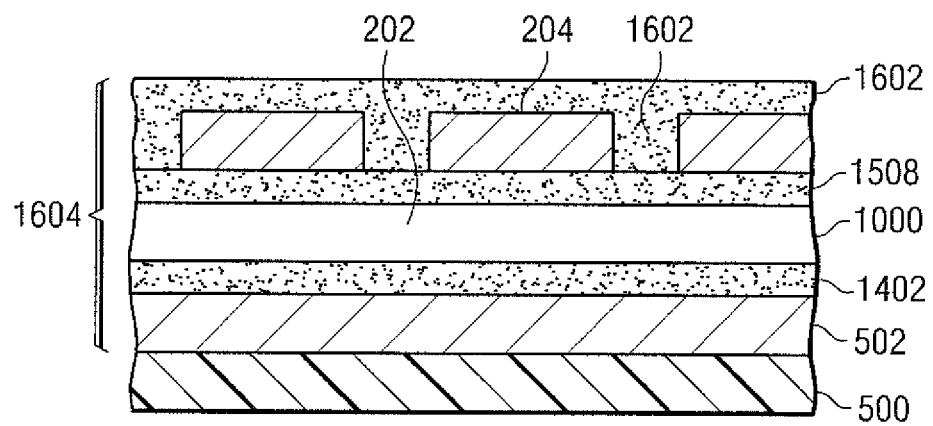
FIG. 16A is an enlarged cross-sectional view of the in-progress balloon wall overlying the mandrel looking in the circumferential direction taken along line 16A-16A of FIG. 16.
Figure 16B:
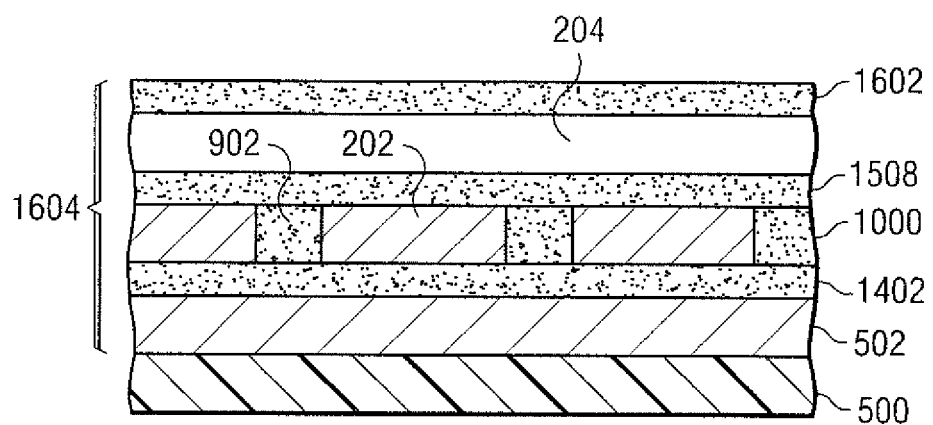
FIG. 16B is an enlarged cross-sectional view of the in-progress balloon wall overlying the mandrel looking in the longitudinal direction taken along line 16B-16B of FIG. 16.

Referring now to FIG. 16, 16A and 16B, a third coating 1602 may be applied to the surface of the illustrated balloon lay-up 1600, which now includes both the hoop (i.e., circumferential) reinforcing fibers 204 and the longitudinal reinforcing fibers 202. The balloon lay-up 1600 is supported by the underlying mandrel 500, which remains pressurized at the predetermined internal pressure $P_1$ to maintain its size and shape. The third coating 1602 may facilitate holding the hoop fibers 204 in position and smoothing the surface of the balloon. In some embodiments, the third coating 1602 is applied to the entire surface of the balloon lay-up 1600. The third coating 1602 is preferably applied by spraying, but may be applied by brushing, dipping or other means. The third coating 1602 will ultimately become the third coating region 216 of the matrix 206, therefore it must be compatible for thermal-welding to the other materials in the matrix. In one embodiment, the third coating 1602 may be formed of a soluble nylon material having a thickness of about 0.0003 inches. Such a third coating 1602 may be thermal-welding compatible with the second coating 1508 (where present) when formed of nylon and with the thermally-weldable material 902 of the underlying sock sheet 1000 when formed of nylon.

Referring now specifically to FIGS. 16A and 16B, after applying the third coating 1602, the in-progress wall 1604 of the balloon 100 is illustrated on the outer surface of the mandrel 500.

Figure 17:
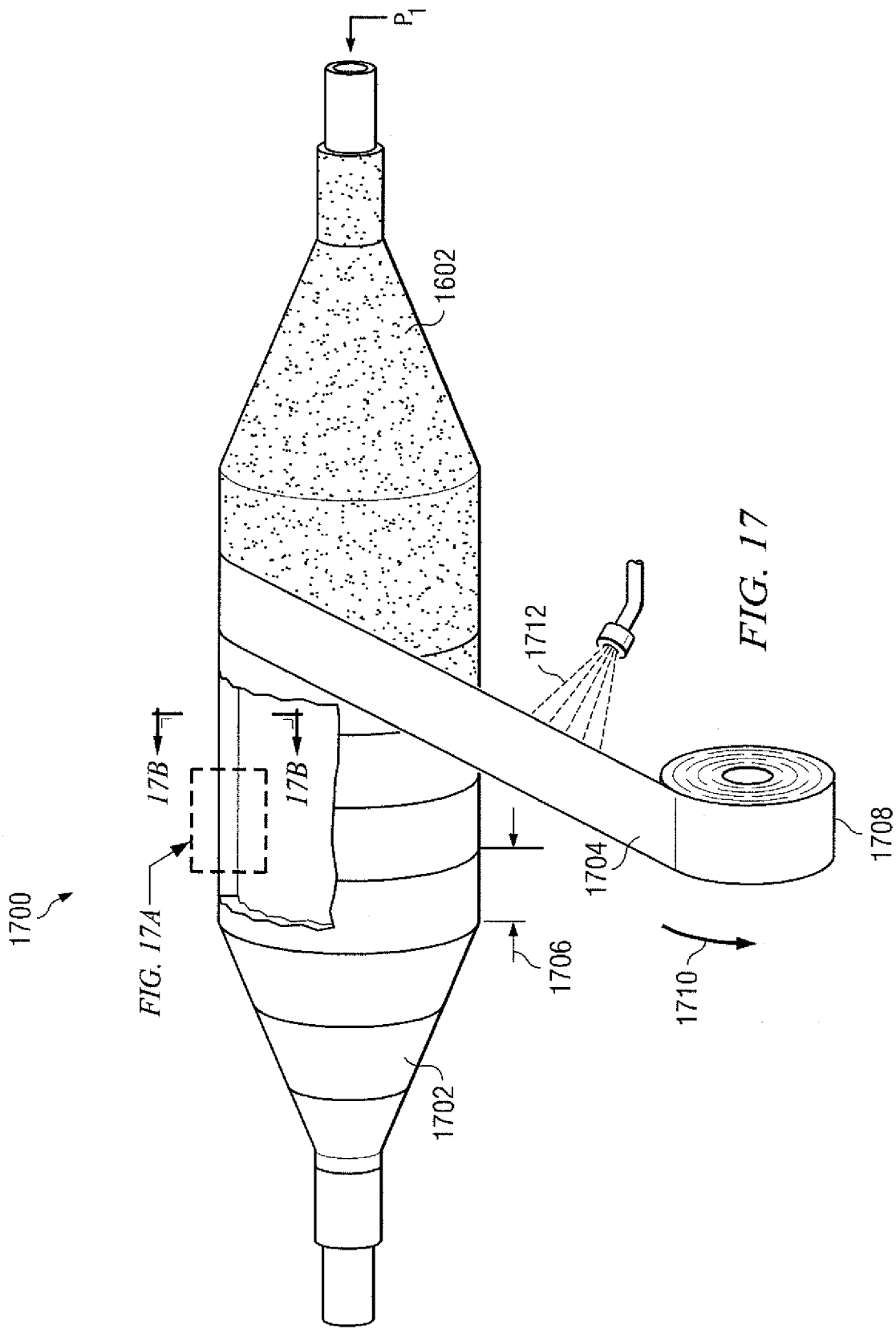
FIG. 17 illustrates wrapping an outer layer over the in-progress balloon and mandrel in accordance with additional embodiments.
Figure 17A:
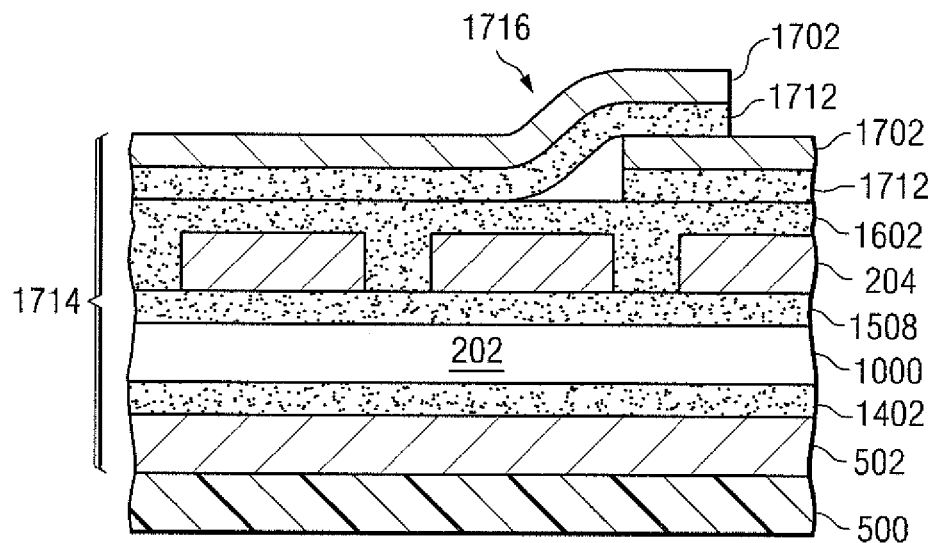
FIG. 17A is an enlarged cross-sectional view of the in-progress balloon wall overlying the mandrel looking in the circumferential direction taken along line 17A-17A of FIG. 17.
Figure 17B:
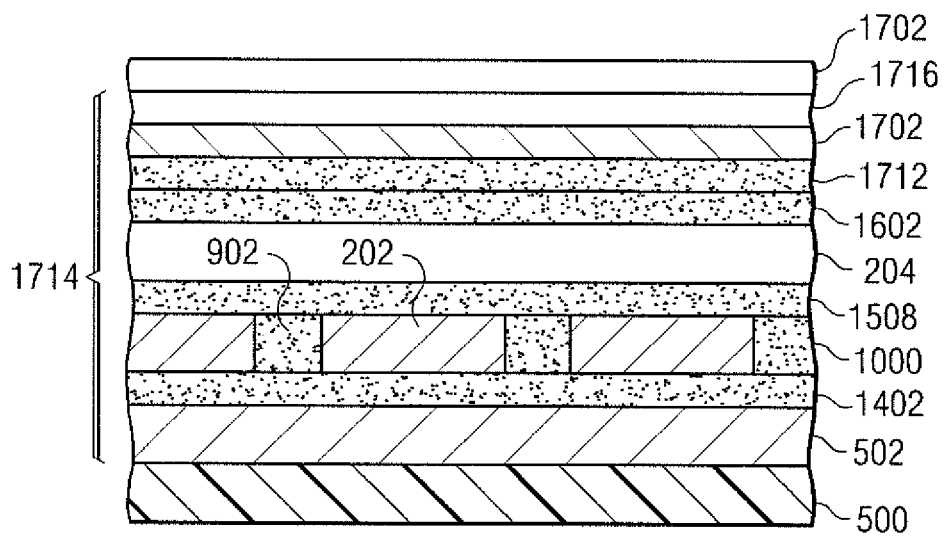
FIG. 17B is an enlarged cross-sectional view of the in-progress balloon wall overlying the mandrel looking in the longitudinal direction taken along line 17B-17B of FIG. 17.

Referring now to FIG. 17, 17A and 17B, an outer layer 1702 may be affixed over the illustrated balloon lay-up 1700, which now includes the third coating 1602. The balloon lay-up 1700 is supported by the underlying mandrel 500, which remains pressurized at the predetermined internal pressure $P_1$ to maintain its size and shape. The outer layer 1702 may provide additional material to increase the puncture-resistance and surface smoothness of the balloon 100. In some embodiments, the outer layer 1702 may comprise a thermally-weldable polymer material. The outer layer 1702 preferably comprises the same material as the balloon matrix 206 or material compatible with the material of balloon matrix. Preferably the outer layer 1702 is formed from the same material as the conformal layer 502. Thus, when the conformal layer 502 is formed from PEBA thermoplastic elastomer, the outer layer 1702 is preferably formed from the same material. In a preferred embodiment, the outer layer may be formed of PEBA, e.g., Pebax®.

In the illustrated embodiment, the outer layer 1702 may comprise a thermally-weldable polymer tape or film 1704 that may be wrapped circumferentially around the balloon lay-up 1700 at a predetermined pitch 1706. In one embodiment, the pitch 1706 may be smaller than the width of the tape 1704 such that successive winds may overlap. The outer layer tape 1704 may be supplied from a storage drum 1708 or other source. In preferred embodiments, the tape 1704 may be wound continuously around the balloon lay-up 1700 from one neck to the opposite neck. In the illustrated embodiment, the circumferential winding (denoted by arrow 1710) is accomplished by revolving the storage drum 1708 around the balloon lay-up 1700, however in other embodiments the balloon lay-up and mandrel 500 may be rotated. For balloons 100 in the 4 to 12 French Unit size, the outer layer 1702 may be formed of PEBA, e.g., Pebax®, having a thickness of about 0.0003 inches. Such small thickness may be obtained by stretching PEBA tape having an original thickness of about 0.0005 inches.

Prior to affixing the outer layer 1702 onto the balloon lay-up 1700, a fourth coating 1712 of thermally-weldable matrix material may be applied to the underside surface of the outer layer material 1704 to facilitate its retention. The fourth coating 1712 is preferably applied by spraying, but may be applied by brushing, dipping or other means. The fourth coating 1712 will ultimately become the fourth coating region 218 of the matrix 206, therefore it must be compatible for thermal-welding to the other materials in the matrix. In one embodiment, the fourth coating 1712 may be formed of a soluble nylon material having a thickness of about 0.0003 inches. Such a fourth coating 1712 may be thermal-welding compatible with the third coating 1602 when formed of nylon and with the outer layer 1702 when formed of PEBA, e.g., Pebax®. It will be appreciated that the outer layer 1702 may not be welded or permanently joined to the balloon lay-up at this time. It is only necessary that the outer layer 1702 be affixed firmly enough to stay in position during further processing.

Referring now specifically to FIGS. 17A and 17B, after affixing the outer layer 1702, the final lay-up wall 1714 of the balloon 100 is illustrated on the outer surface of the mandrel 500. In the embodiment illustrated, the fourth coating 1712 has been applied as previously described. The overlapping of the tape 1704 is shown at arrow 1716.

Figure 19:
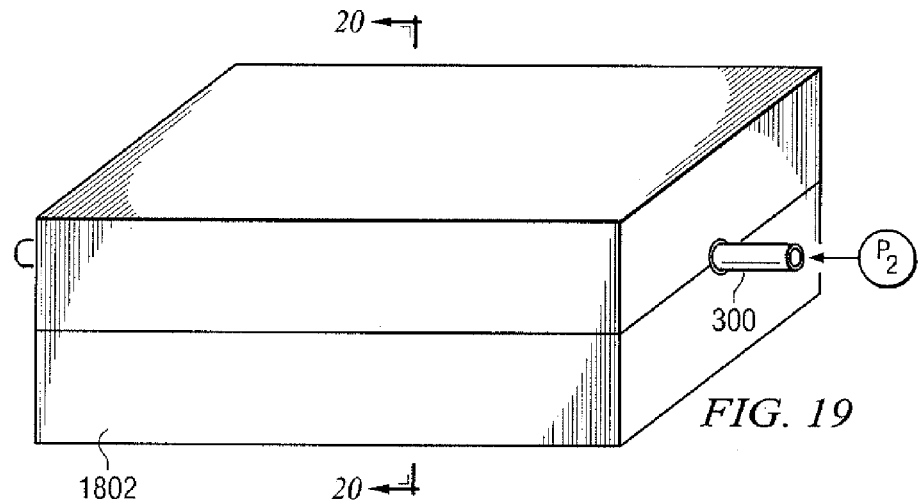
FIG. 19 show the die of FIG. 18 closed over the final balloon lay-up and mandrel prior to thermal welding.
Figure 20:
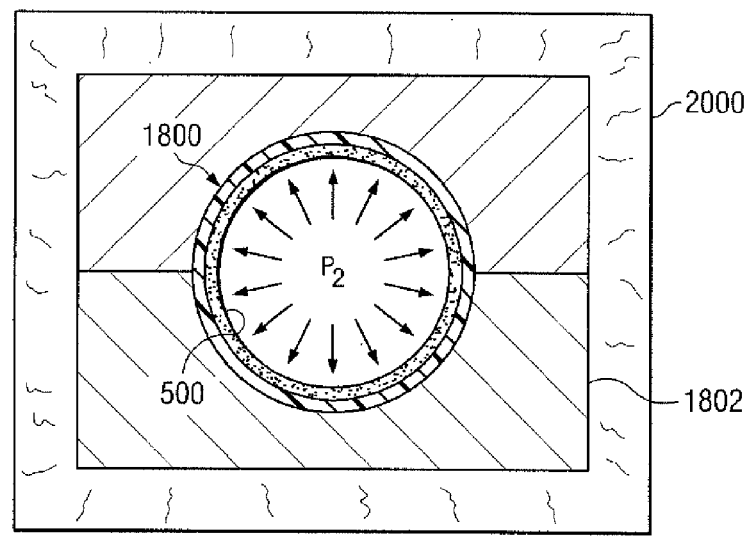
FIG. 20 is a cross-sectional view taken in the direction of line 20-20 of FIG. 19 showing the die, final balloon lay-up and mandrel being heated in a oven in accordance with additional embodiments.

Referring now to FIGS. 18, 19 and 20, there is illustrated the thermal welding of the final balloon lay-up 1800 following application of the outer layer 1702 described above. Referring first to FIG. 18, the final lay-up 1800 (with the mandrel 500 still inside) may be placed inside a die 1802 having a balloon-shaped cavity 1804. Passages 1806 may be provided in die 1802 so that the mandrel tube 300 may extend outside to allow pressurization while the lay-up is in the die.

Referring now to FIG. 19, after the final balloon lay-up 1800 is placed in the die cavity 1804, the die 1802 may be closed and secured. Next, heat and pressure are applied to thermally weld the components of the balloon lay-up into the final balloon 100.

Referring now to FIG. 20, in one embodiment the die 1802 containing the final balloon lay-up 1800 is placed inside an oven 2000 for heating (for purposes of illustration, the wall of the final lay-up 1800 is shown in simplified form in FIG. 20). In other embodiments, a die having integral heating may be used. While inside the die, the mandrel 500 may be internally pressurized to a predetermined pressure $P_2$. Since the mandrel 500 is semi-compliant, the internal pressure $P_2$ will force the mandrel walls outward, pressing each wall 1714 of the final lay-up 1800 against the heated walls of the die cavity 1804. In some embodiments, the die 1802 may be heated before the mandrel 500 is pressurized. In other embodiments, the mandrel 500 may be pressurized before the die 1802 is heated. In still other embodiments, the heating of the die and the pressurization of the mandrel 500 may occur simultaneously. Predetermined conditions of heat and pressure maintained inside the die 1820 for a predetermined time period may weld together the thermally-weldable components of the final lay-up wall 1714 (FIGS. 17A and 17B), thereby forming the finished balloon wall 200 (FIGS. 2A and 2B). In one embodiment, a final balloon lay-up 1800 comprising reinforcing fibers 202, 204 made of Technora® brand para-aramid layered with nylon and Pebax® brand PEBA component layers may be thermally welded by heating the die 1802 to about 300 degrees F., pressurizing the mandrel 500 to about 150 psi, and maintaining these conditions for a period of about 2 minutes.

During the thermal welding process, the thermally-weldable materials in the wall 1714 of the final lay-up 1800 may fuse to one another forming a continuous matrix 206 of the finished balloon wall 200 (FIGS. 2A and 2B). In preferred embodiments, the matrix 206 may be continuous and free of adhesive materials. In some embodiments, the thermally-weldable materials in the wall 1714 of the final lay-up may plastically deform under heat and pressure to fill any voids (e.g., in-between and around the reinforcing fibers) such that the reinforcing fibers 202 and 204 are fully encapsulated by the matrix 206 in the finished balloon 100. In some embodiments, the thermally-weldable materials in the wall 1714 of the final lay-up may plastically deform under heat and pressure to even-out surface irregularities (e.g., the tape overlap 1716) such that the outer surface 230 of the finished balloon wall 200 is very smooth. In some embodiments, the thermally-weldable materials in the wall 1714 of the final lay-up may weld together, plastically deform and/or be compressed under heat and pressure such that the overall thickness of the finished balloon wall 200 is significantly less than the thickness of the wall 1714.

After thermal welding is complete, the die 1802 may be cooled, the pressure in the mandrel 500 may be reduced, and the balloon 100 (still overlying the mandrel 500) may be removed from the die cavity. The walls of the mandrel 500 mandrel walls may then be collapsed by releasing the internal pressure or applying a partial vacuum via the tube 300.

Figure 21:
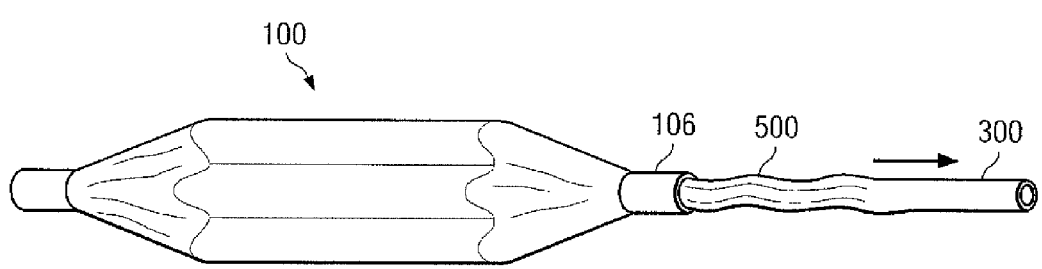
FIG. 21 is a perspective view of the collapsed mandrel being removed from the finished medical balloon after thermal welding in accordance with additional embodiments.

Referring now to FIG. 21, after collapsing the walls of the mandrel 500 inside the balloon 100, the mandrel itself may be removed from the balloon by pulling it through the neck 106 of the balloon by means of tube 300. The balloon 100 is now complete (FIGS. 1 and 2) and ready for inspection and testing or further processing, e.g., attachment to a catheter.

It will be appreciated by those skilled in the art having the benefit of this disclosure that this non-compliant medical balloon may provide improved flexibility, simplified assembly, reduced folding wall thickness and/or more uniform wall thicknesses. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A medical balloon having a longitudinal axis, comprising,
    an inner layer of thermally-weldable polymer material;
    a first fiber/polymer matrix layer disposed over the inner layer, the first fiber/polymer matrix layer comprising a plurality of substantially inelastic fibers running substantially parallel to one another and substantially parallel to the longitudinal axis of the balloon, the polymer of the first fiber/polymer matrix layer being a thermally-weldable polymer material;
    a second fiber/polymer matrix layer disposed over the first fiber/polymer matrix layer, the second fiber/polymer matrix layer comprising at least one substantially inelastic fiber winding circumferentially around the longitudinal axis of the balloon, the polymer of the second fiber/polymer matrix layer being a thermally-weldable polymer material;
    an outer layer of thermally-weldable polymer material disposed over the second fiber/polymer matrix layer.

2. The balloon according to claim 1, wherein the thermally-weldable polymer materials from each of the layers is fused together into a continuous polymer matrix encapsulating the fibers of the first and second fiber/polymer matrix layers and defining a barrel wall, cone walls and neck walls of the balloon.

3. The balloon according to claim 2, wherein the fibers of the first fiber layer have a pattern of different lengths and are divisible into a first group and a second group based on length.

4. The balloon according to claim 3, wherein each fiber of the first group begins in the neck wall at one end of the balloon, extends longitudinally and terminates in the neck wall at the opposite end of the balloon; and each fiber of the second group begins in the cone wall at one end of the balloon, extends longitudinally and terminates in the cone wall at the opposite end of the balloon.

5. The balloon according to claim 4, wherein the length of the fibers of the second group varies progressively in accordance to their proximity to the fibers of the first group, the fibers of the second group closest to the fibers of the first group being longer than the fibers of the second group further from the fibers of the first group.

6. The balloon according to claim 1, further including a removable mandrel for supporting the inner layer of thermally weldable material.

7. The balloon according to claim 6, wherein the mandrel comprises a non thermally weldable material.

\* \* \* \* \*